(12) United States Patent
Yoon

(10) Patent No.: US 6,228,068 B1
(45) Date of Patent: May 8, 2001

(54) EXPANDABLE ENDOSCOPIC PORTAL AND METHODS THEREFOR

(76) Inventor: InBae Yoon, 2101 Highland Ridge Dr., Phoenix, MD (US) 21131

( * ) Notice: Subject to any disclaimer, the term of this patent is extended or adjusted under 35 U.S.C. 154(b) by 0 days.

(21) Appl. No.: 09/243,114

(22) Filed: Feb. 3, 1999

Related U.S. Application Data

(62) Division of application No. 08/651,284, filed on May 22, 1996, now Pat. No. 5,882,345.

(51) Int. Cl.$^7$ ...................................... A61M 5/00
(52) U.S. Cl. ......................... 604/246; 604/264; 604/105; 604/523
(58) Field of Search ..................................... 604/105, 904, 604/104, 523, 264, 93, 913, 286, 1–3, 11–19, 164.01, 164.03, 164.09, 164.1, 164.11, 167.01, 167.06, 246; 606/192

(56) References Cited

U.S. PATENT DOCUMENTS

| | | | |
|---|---|---|---|
| Re. 35,312 | * 8/1996 | Christoudias | 600/207 |
| 3,509,883 | 5/1970 | Dibelius . | |
| 3,788,318 | 1/1974 | Kim et al. . | |
| 3,789,852 | 2/1974 | Kim et al. . | |
| 4,177,814 | 12/1979 | Knepshield et al. . | |
| 4,475,548 | 10/1984 | Muto . | |
| 4,555,242 | 11/1985 | Saudagar . | |
| 4,568,326 | * 2/1986 | Rangaswamy | 604/1 |
| 4,601,710 | 7/1986 | Moll . | |
| 4,626,245 | 12/1986 | Weinstein . | |
| 4,655,752 | 4/1987 | Konkanen et al. . | |
| 4,899,729 | 2/1990 | Gill et al. . | |
| 4,917,668 | 4/1990 | Haindl . | |
| 4,946,440 | 8/1990 | Hall . | |
| 5,015,239 | 5/1991 | Browne . | |
| 5,074,840 | * 12/1991 | Yoon | 604/15 |
| 5,104,389 | 4/1992 | Deem et al. . | |
| 5,139,511 | 8/1992 | Gill et al. . | |
| 5,158,553 | 10/1992 | Berry et al. . | |
| 5,176,659 | 1/1993 | Mancini . | |
| 5,183,464 | 2/1993 | Dubrul et al. . | |
| 5,207,656 | 5/1993 | Kranys . | |
| 5,256,150 | 10/1993 | Quiachon et al. . | |
| 5,320,611 | 6/1994 | Bonutti et al. . | |

(List continued on next page.)

Primary Examiner—Anhtuan T. Nguyen
Assistant Examiner—Cris Rodriguez
(74) Attorney, Agent, or Firm—Blank Rome Comisky & McCauley LLP

(57) ABSTRACT

An expandable endoscopic portal for providing a passage through a body cavity wall includes a cannula comprising an absorbent member having a distal end for positioning in the body cavity, a proximal end for positioning external of the body cavity and a passage between the distal and proximal ends for receiving instruments. The absorbent member has a compressed dry state prior to introduction through the cavity wall and an expanded wet state when supplied with fluid upon introduction of the distal end in the body cavity. The absorbent member is rigid in the dry state to facilitate passage through the cavity wall and is soft in the wet state. The absorbent member has an initial cross sectional size in the dry state for introduction through an opening in the cavity wall corresponding in size to the initial cross sectional size. The absorbent member in the wet state has a cross sectional size greater than the initial cross sectional size to dilate the opening and/or form a seal along the thickness of the cavity wall. Instruments of various cross sectional sizes can be introduced in the body cavity through the passage in sealing relation. A method of establishing a passage through a cavity wall includes introducing an elongate absorbent member in an opening in the cavity wall with the absorbent member in a dry state such that the absorbent member extends longitudinally through the cavity wall and hydrating the absorbent member to place the absorbent member in a wet state to cause the absorbent member to expand radially within the opening.

25 Claims, 26 Drawing Sheets

U.S. PATENT DOCUMENTS

| | | |
|---|---|---|
| 5,334,164 | 8/1994 | Guy et al. . |
| 5,360,417 | 11/1994 | Gravener et al. . |
| 5,374,261 * | 12/1994 | Yoon ................................. 604/385.1 |
| 5,389,080 | 2/1995 | Yoon . |
| 5,407,423 | 4/1995 | Yoon . |
| 5,429,609 | 7/1995 | Yoon . |
| 5,441,486 | 8/1995 | Yoon . |
| 5,451,204 * | 9/1995 | Yoon ........................................ 604/1 |
| 5,514,091 * | 5/1996 | Yoon ................................... 604/101 |
| 5,540,658 | 7/1996 | Evans et al. . |
| 5,545,179 | 8/1996 | Williamson, IV . |
| 5,549,826 | 8/1996 | Lapoint, Jr. . |
| 5,556,376 * | 9/1996 | Yoon ..................................... 604/15 |
| 5,593,384 | 1/1997 | Halem . |
| 5,599,305 | 2/1997 | Hermann et al. . |
| 5,755,706 * | 5/1998 | Kronenthal et al. ................. 604/358 |
| 5,814,026 * | 9/1998 | Yoon ................................... 604/280 |
| 5,823,947 * | 10/1998 | Yoon et al. ......................... 600/207 |
| 5,971,960 * | 10/1999 | Flom et al. ......................... 604/174 |
| 6,033,390 * | 3/2000 | Von Dyck ........................... 604/332 |
| 6,053,900 * | 4/2000 | Brown et al. ....................... 604/500 |

* cited by examiner

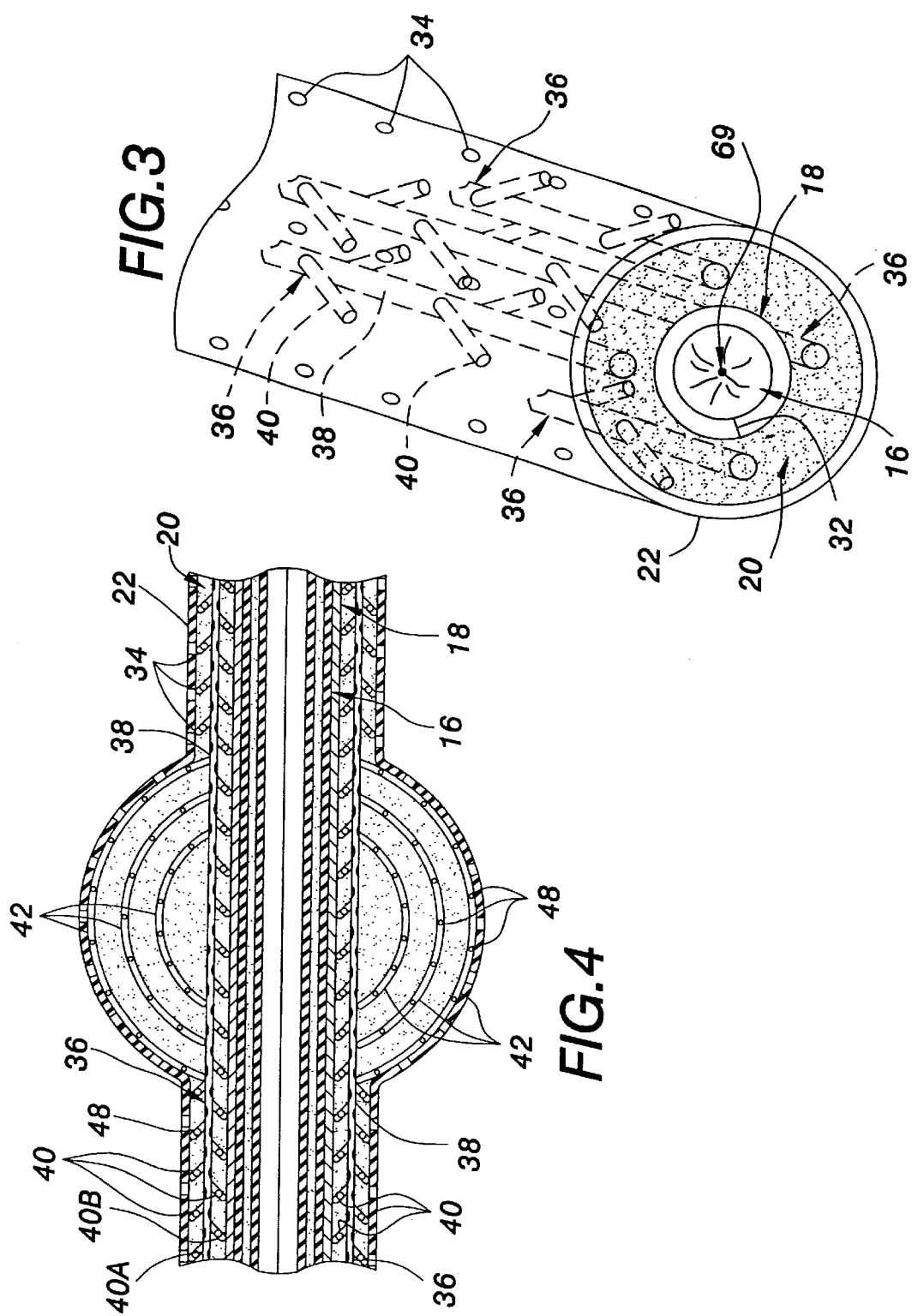

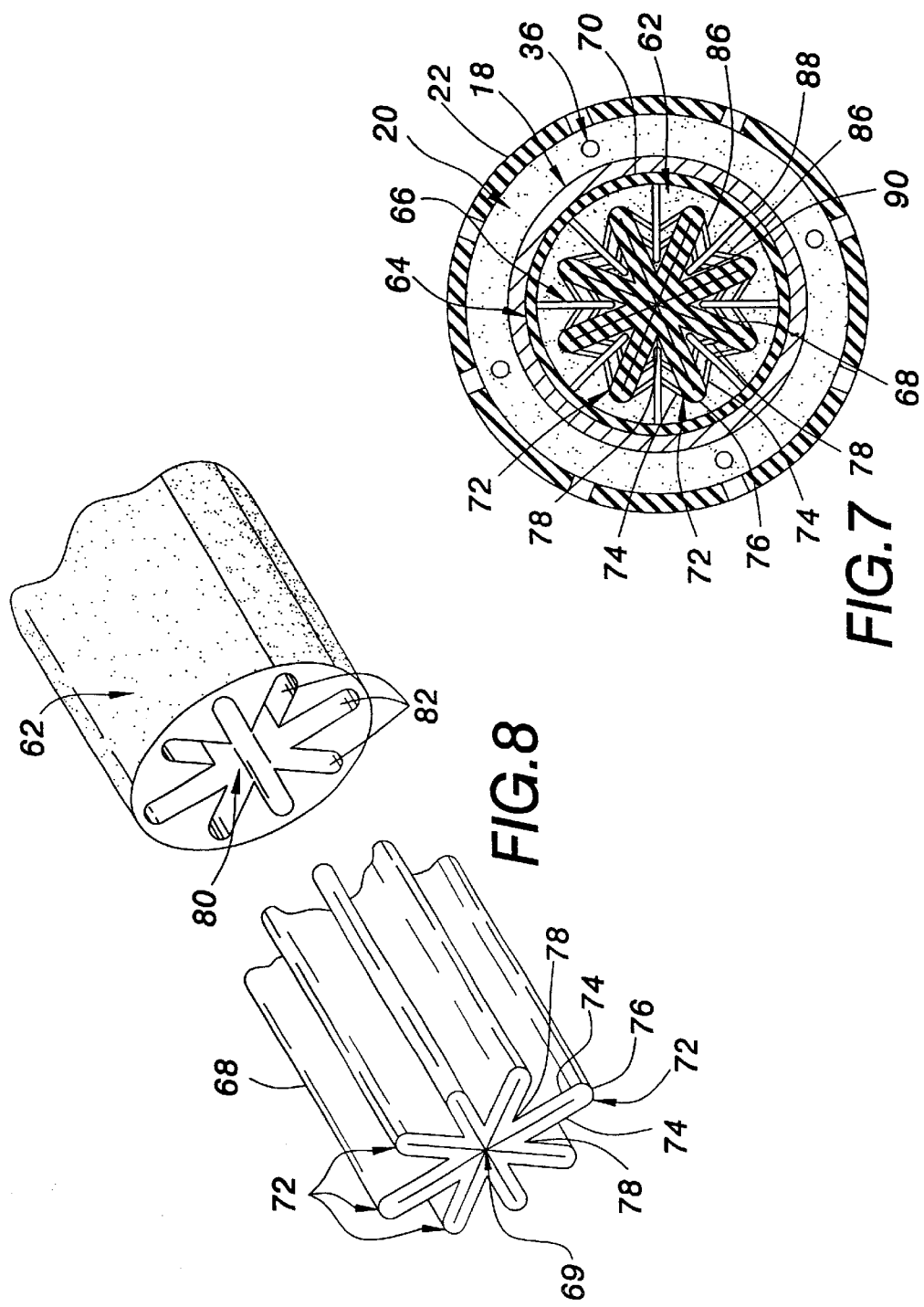

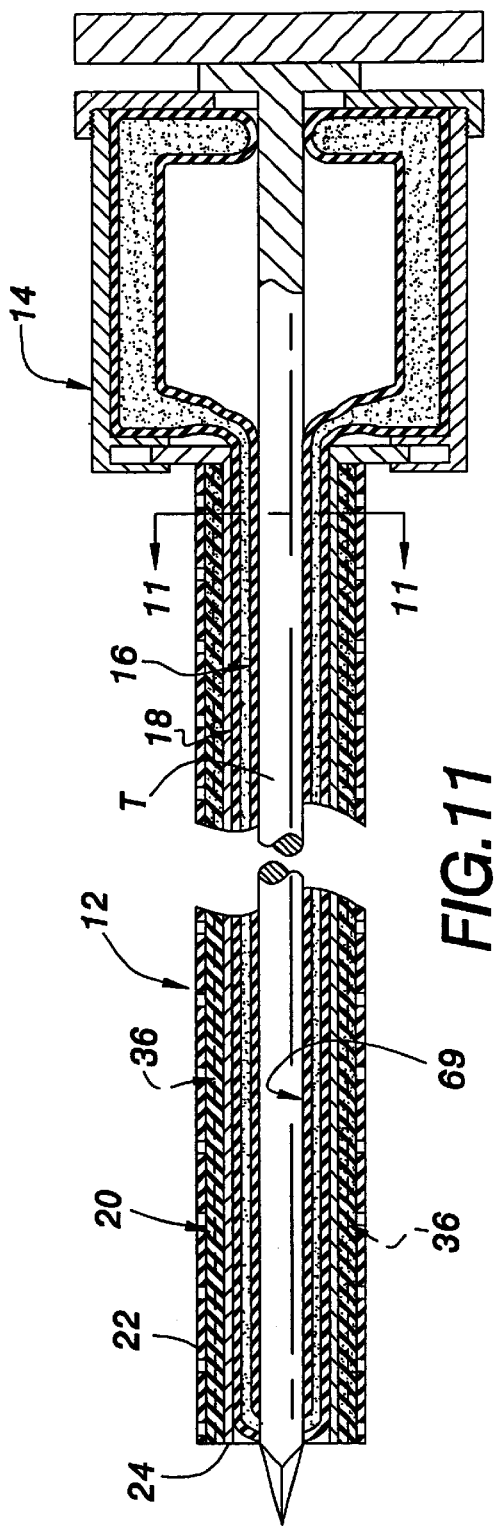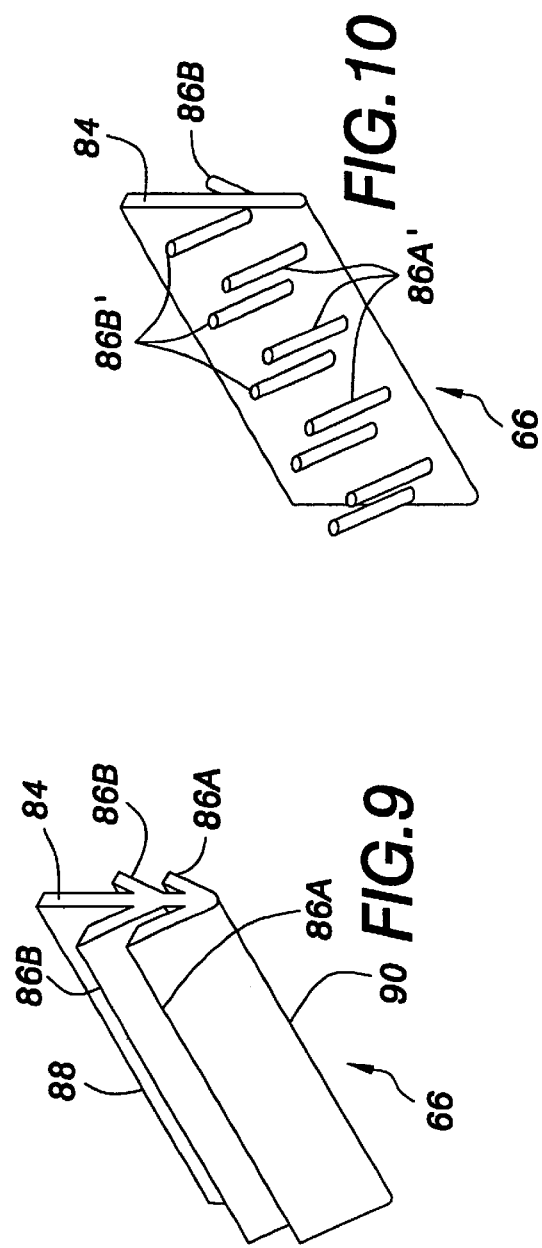

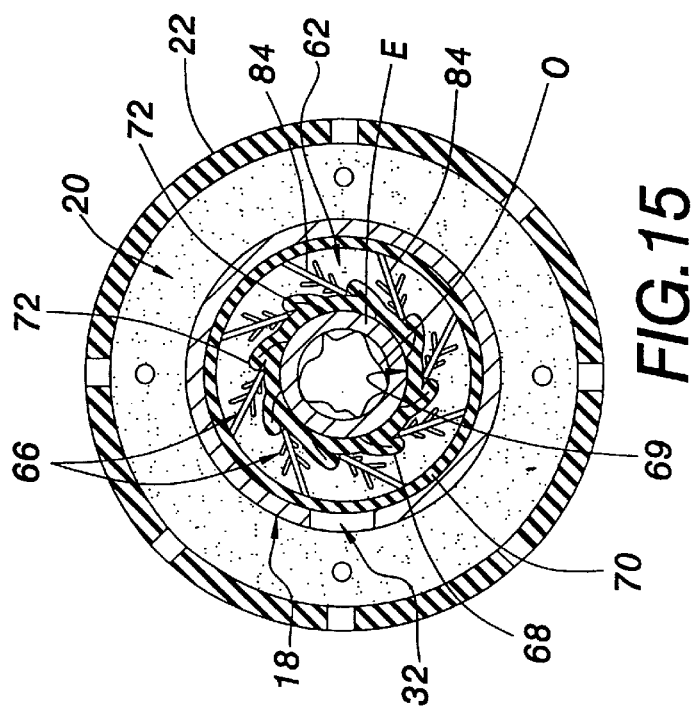
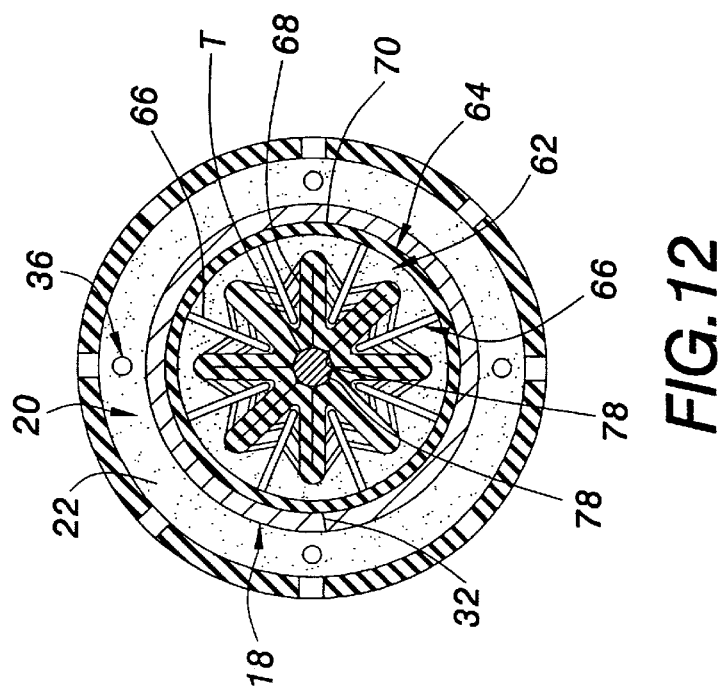

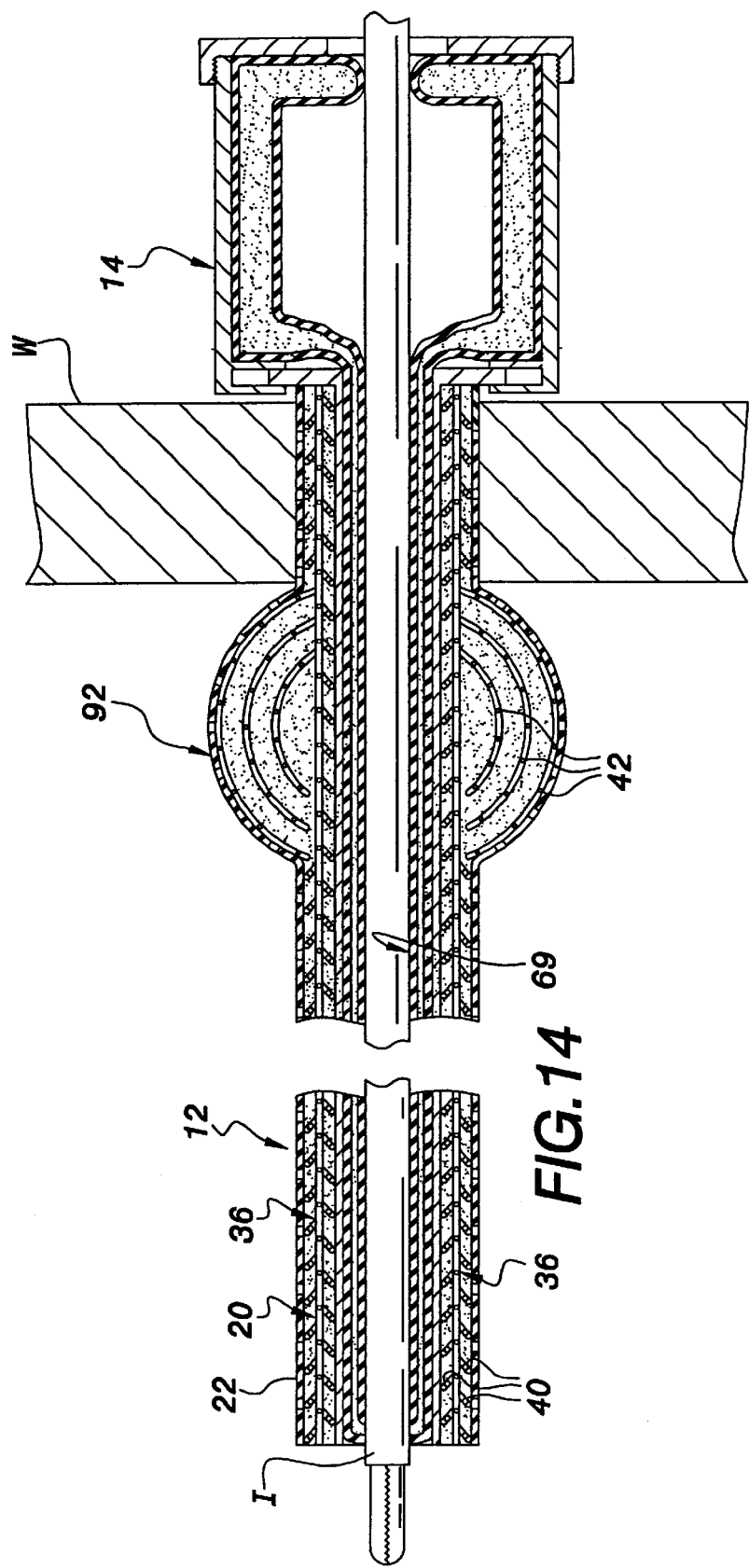

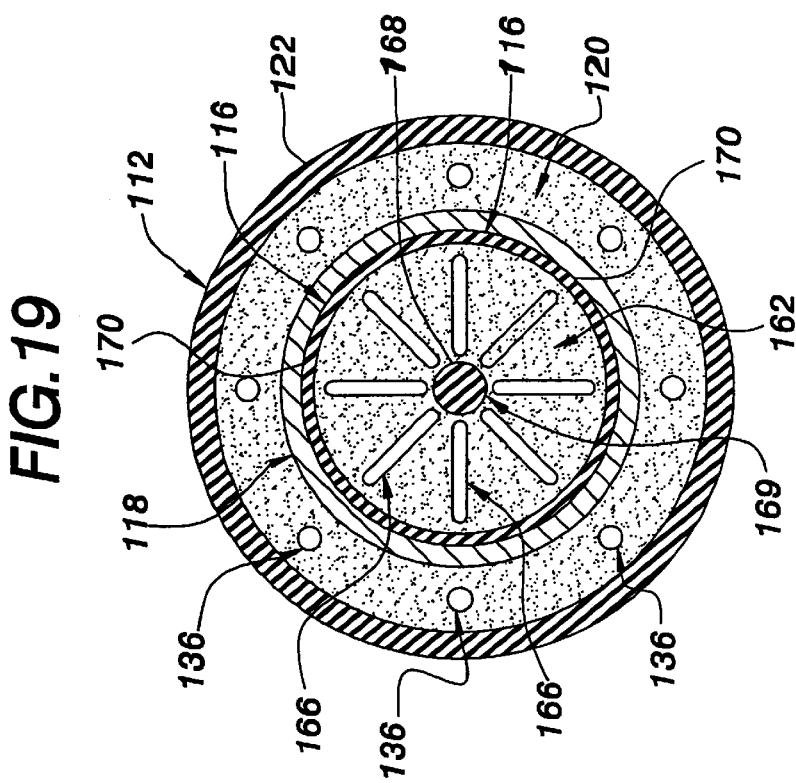
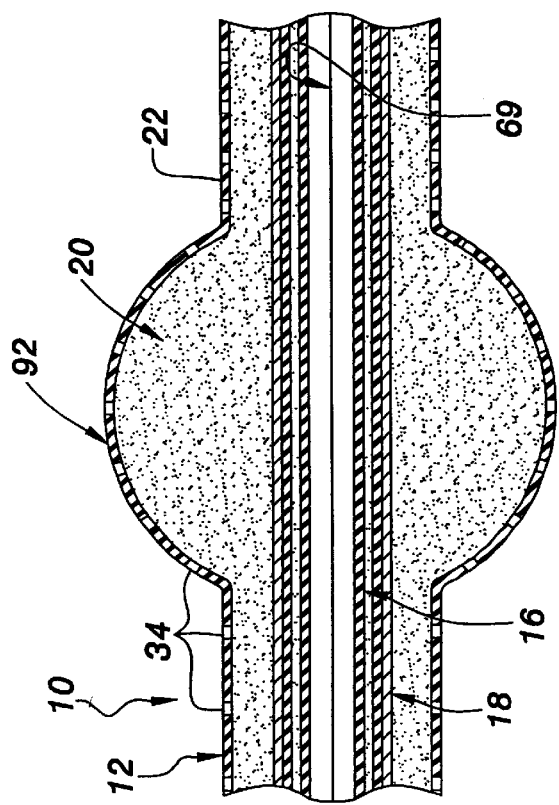

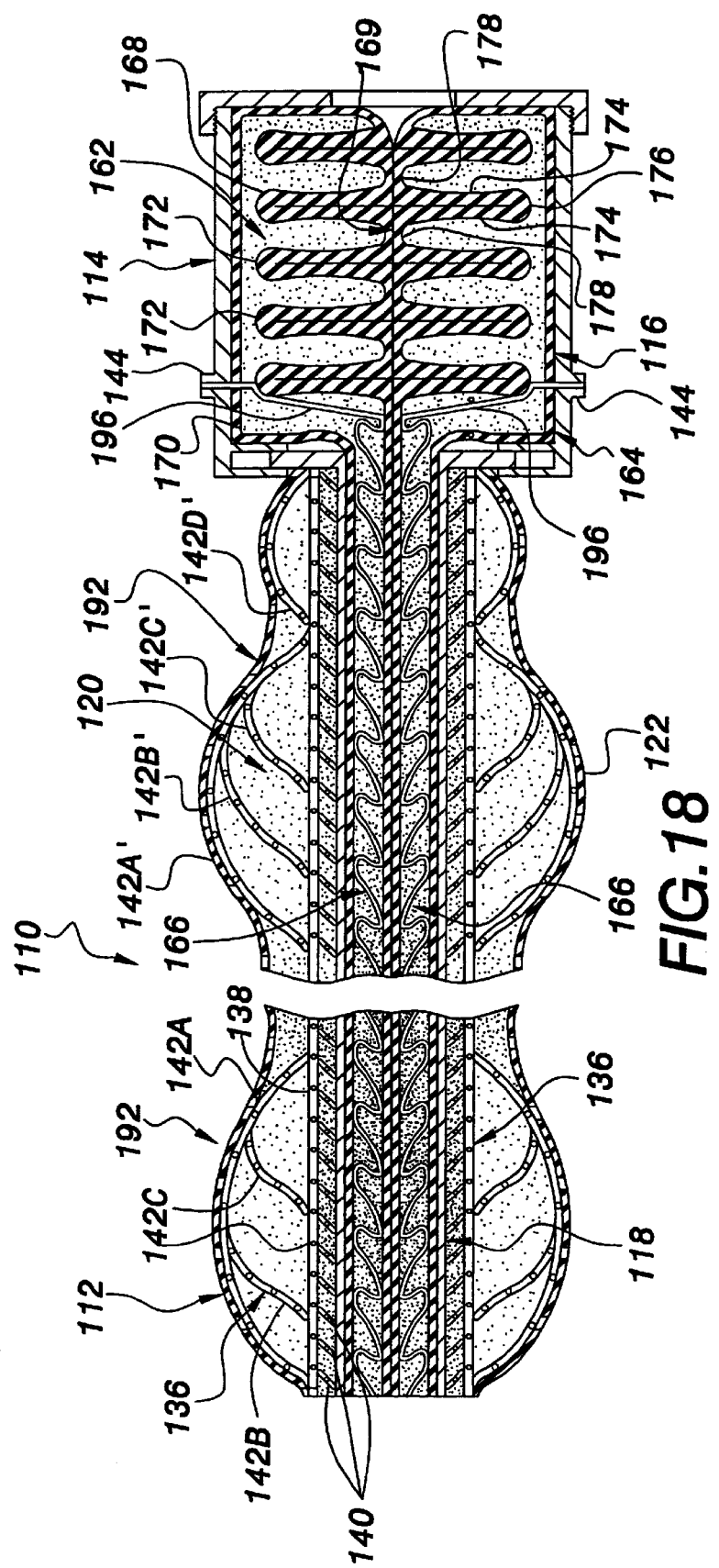

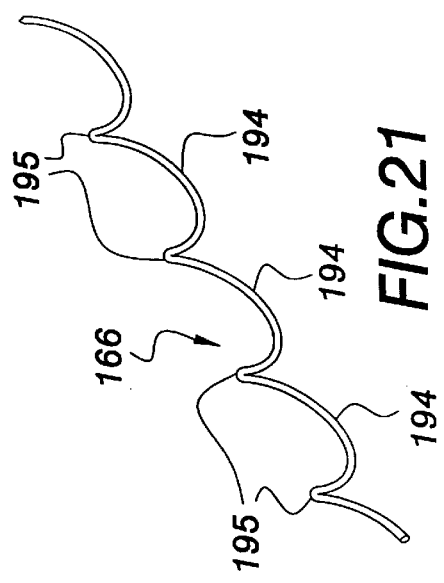
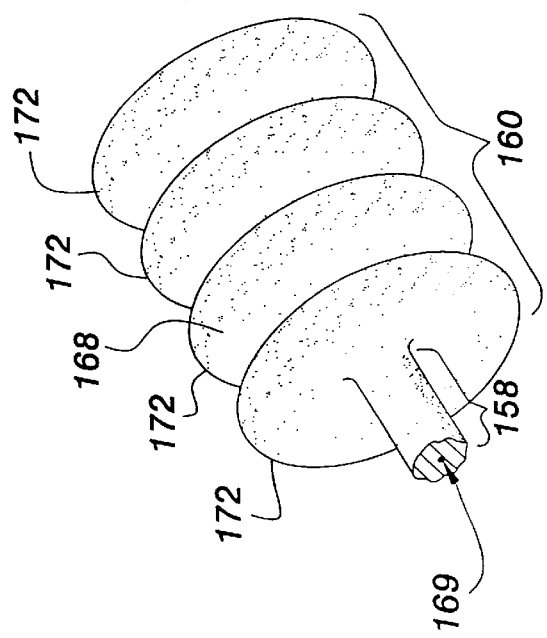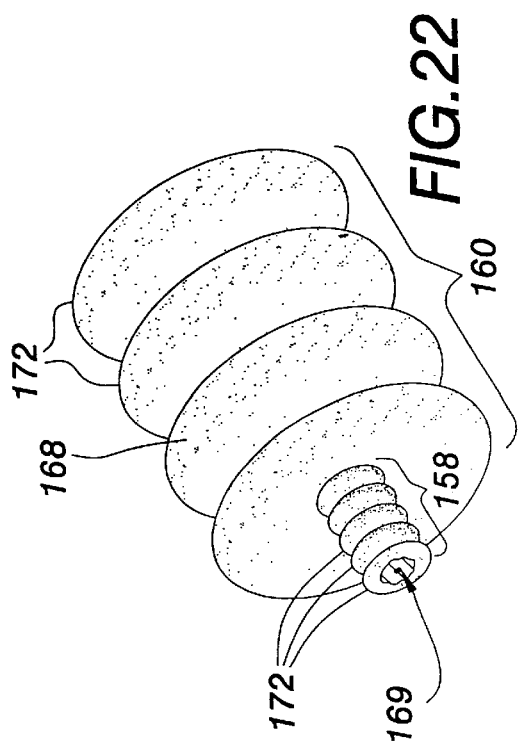

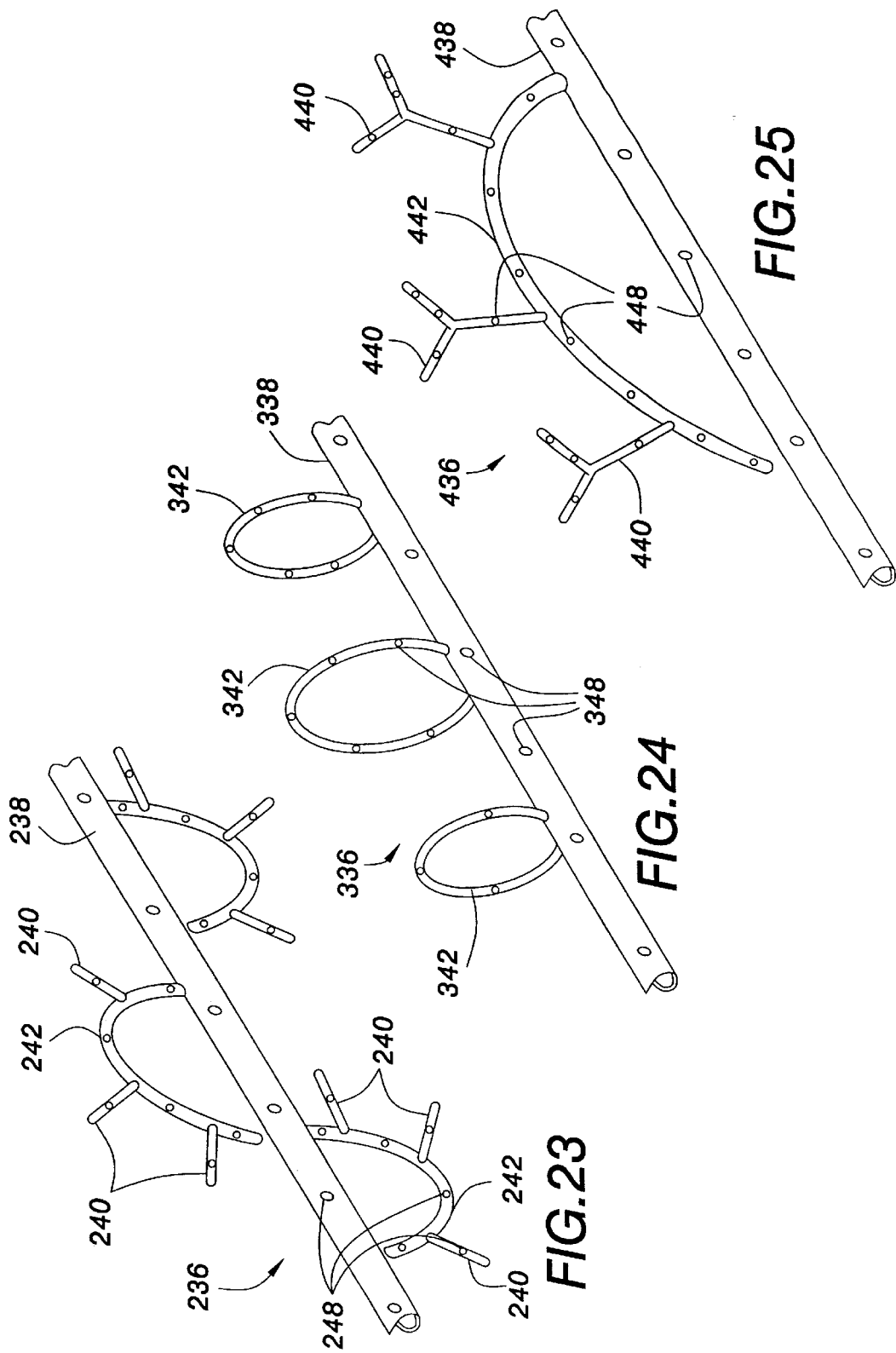

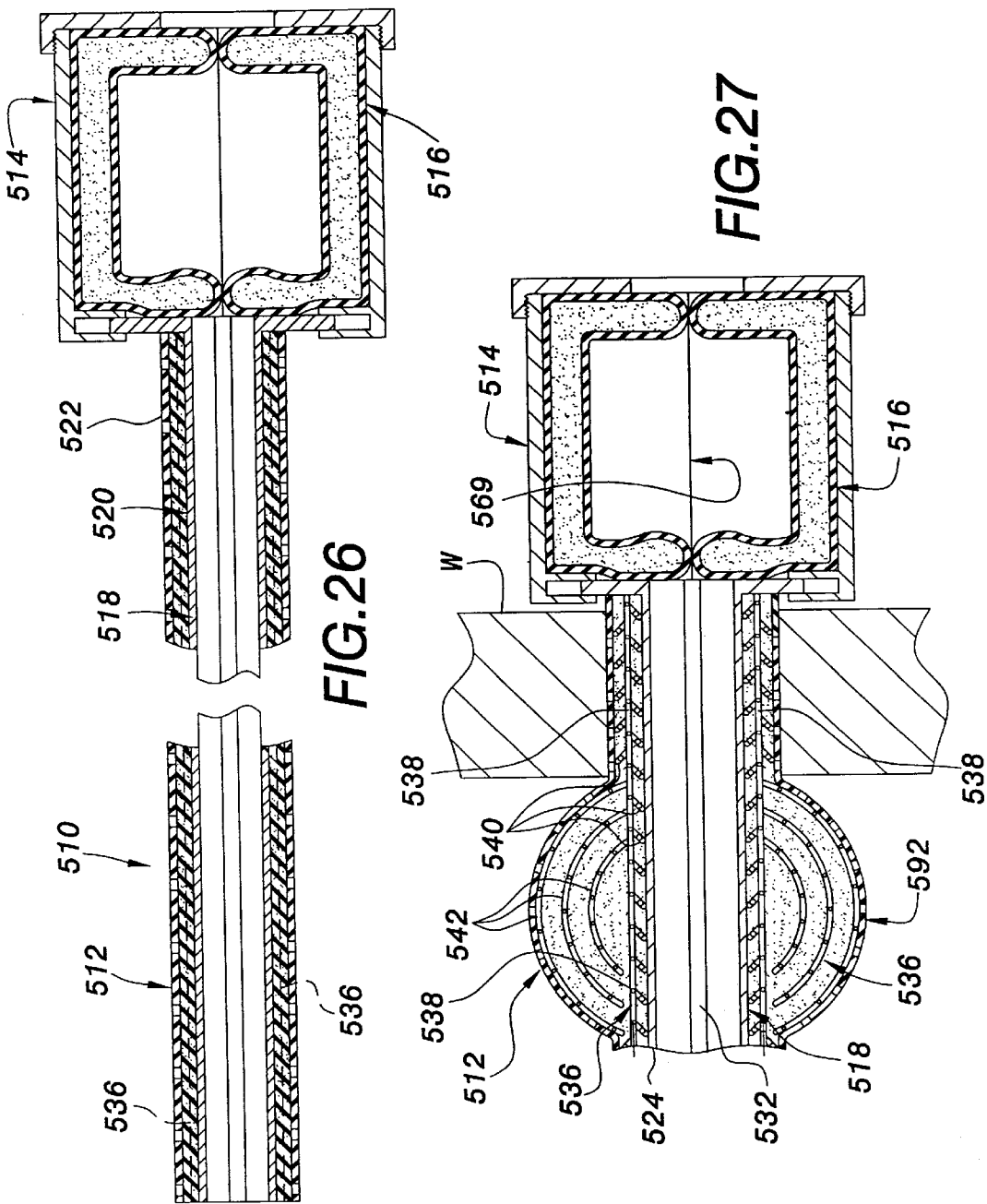

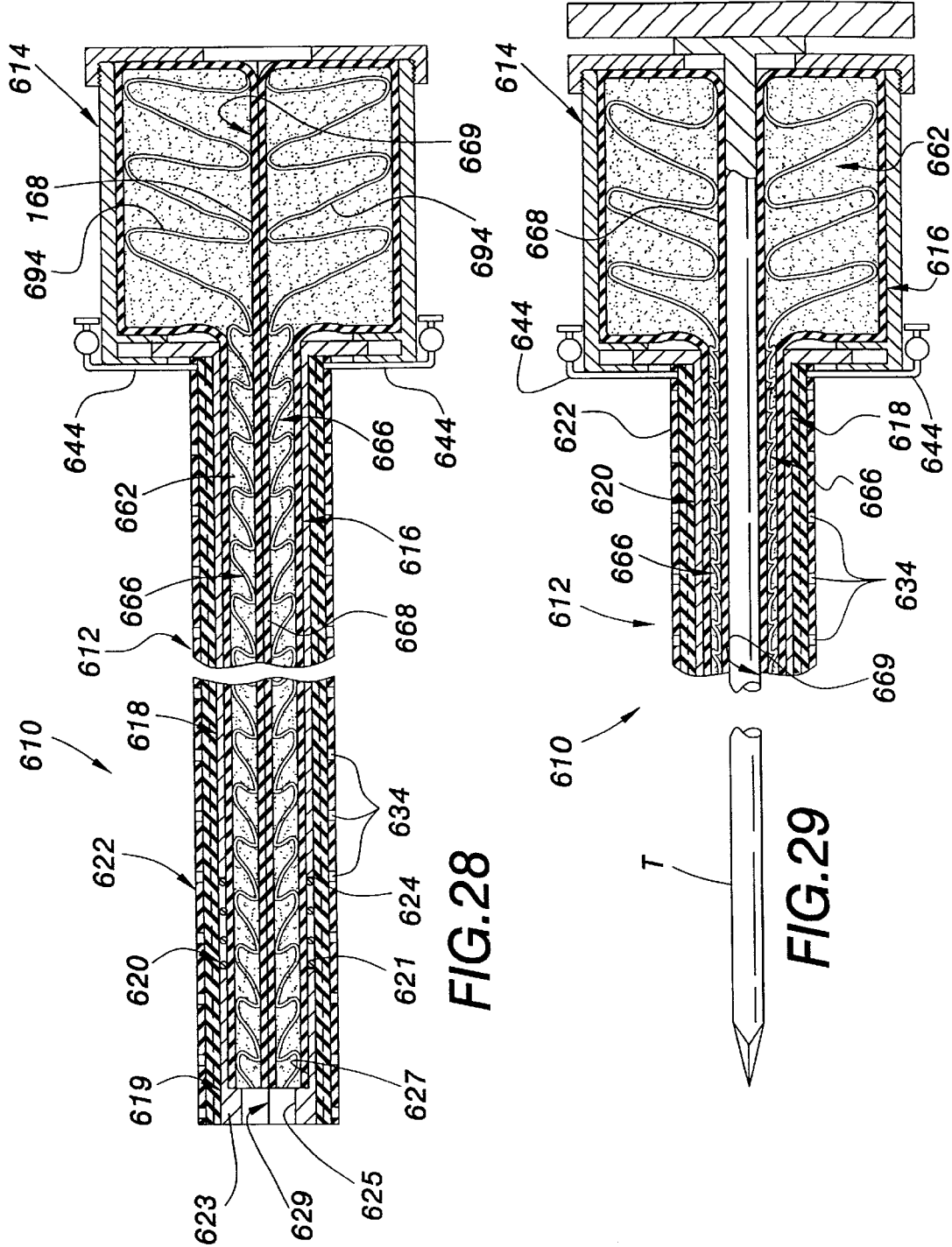

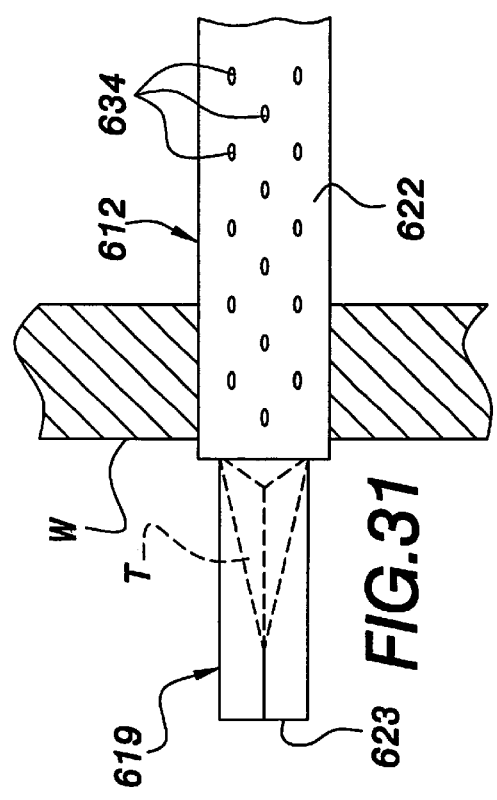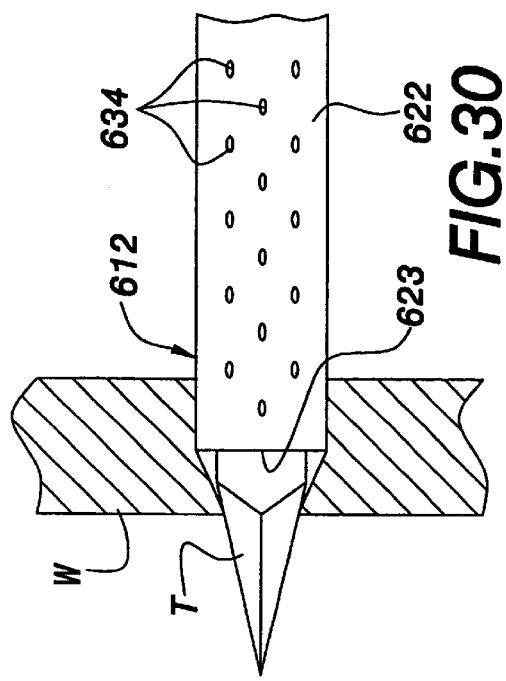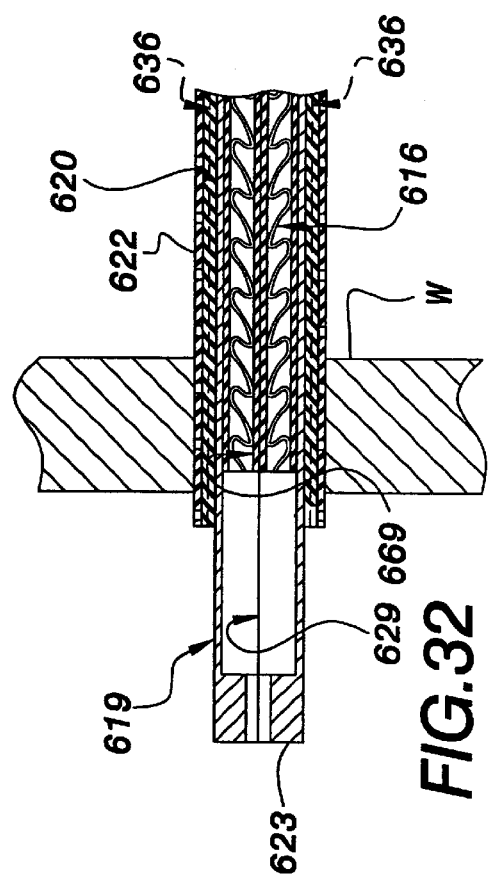

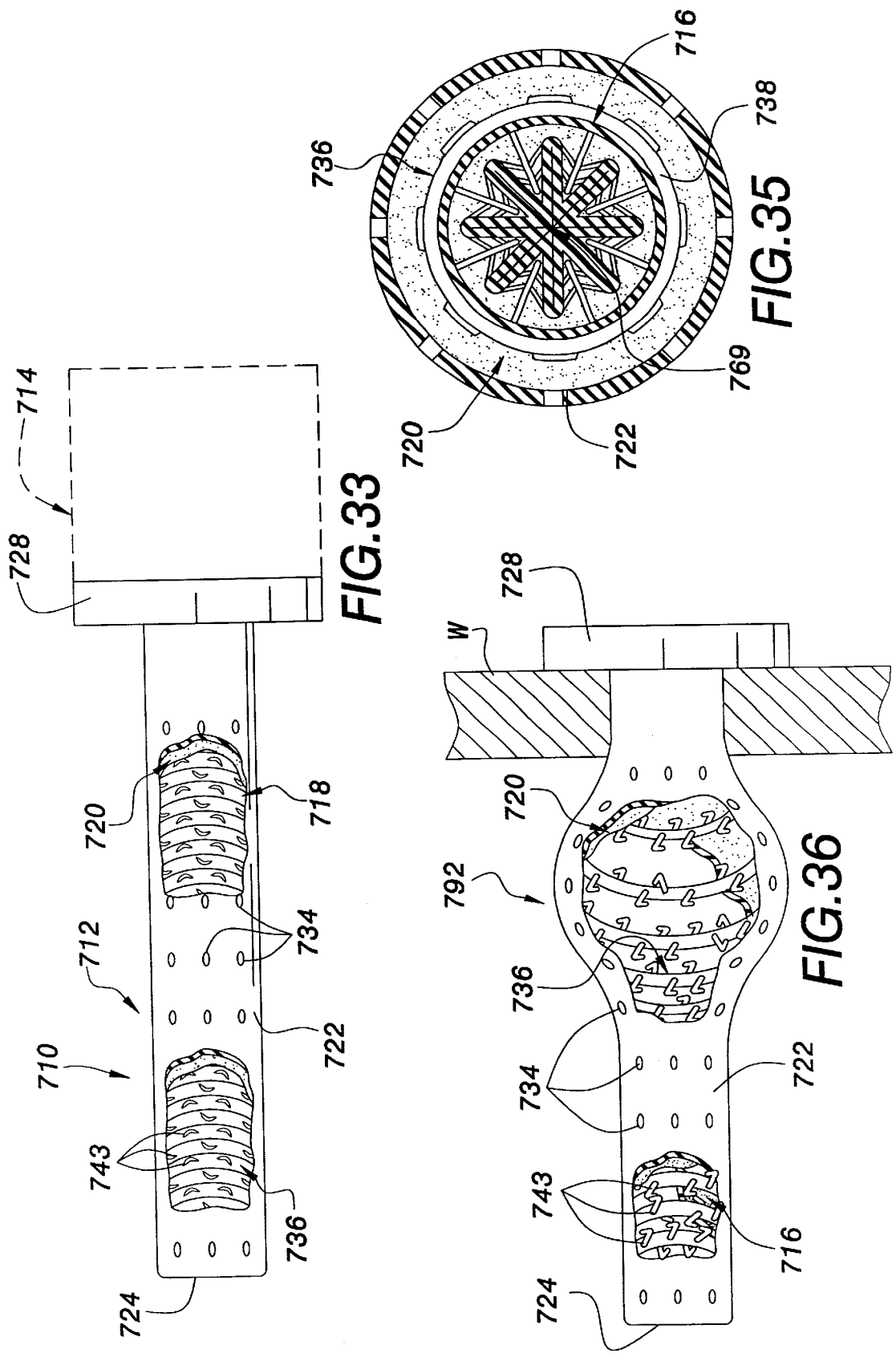

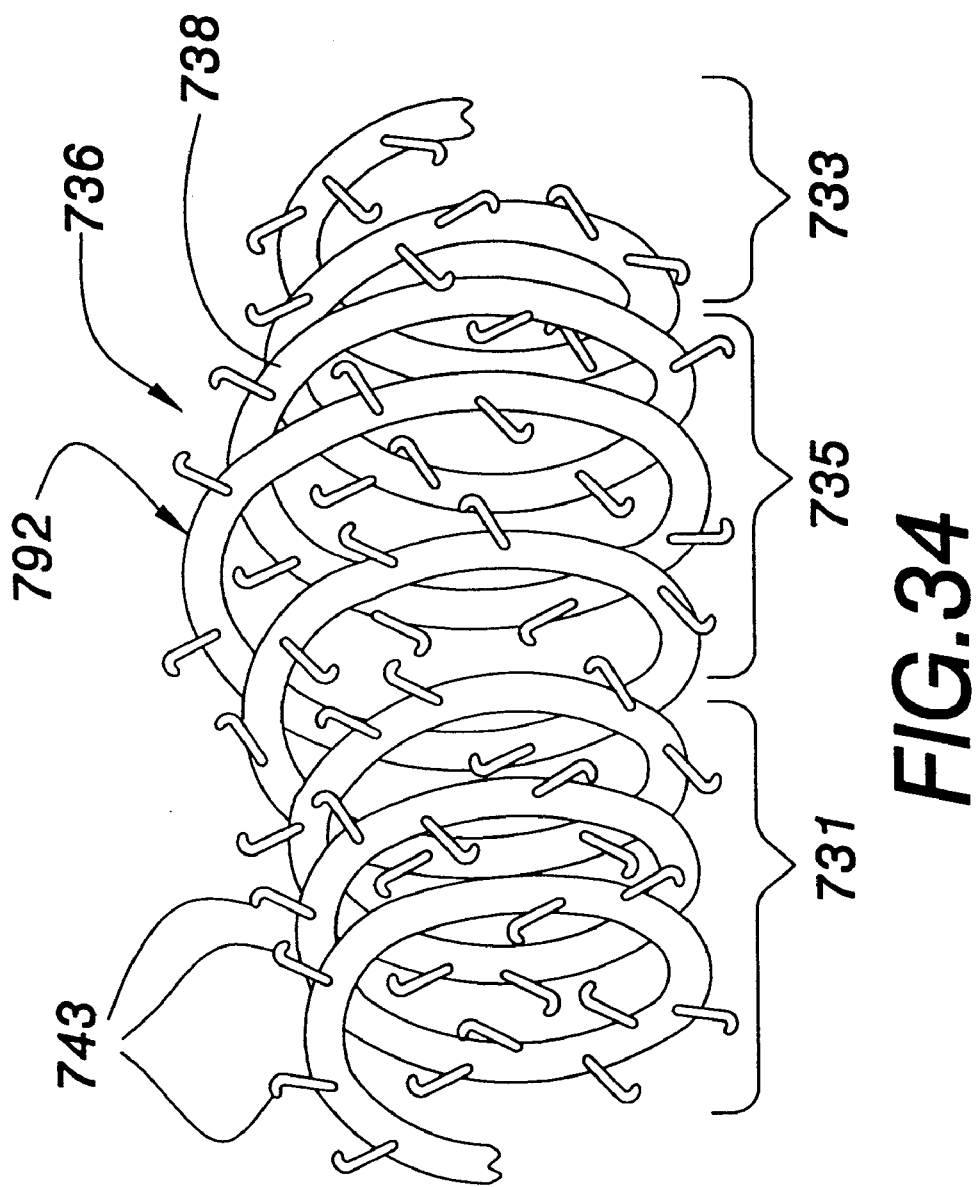

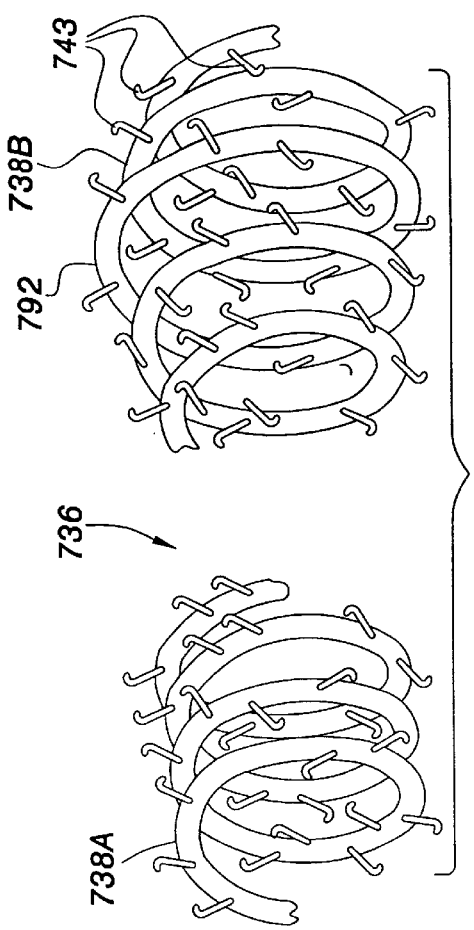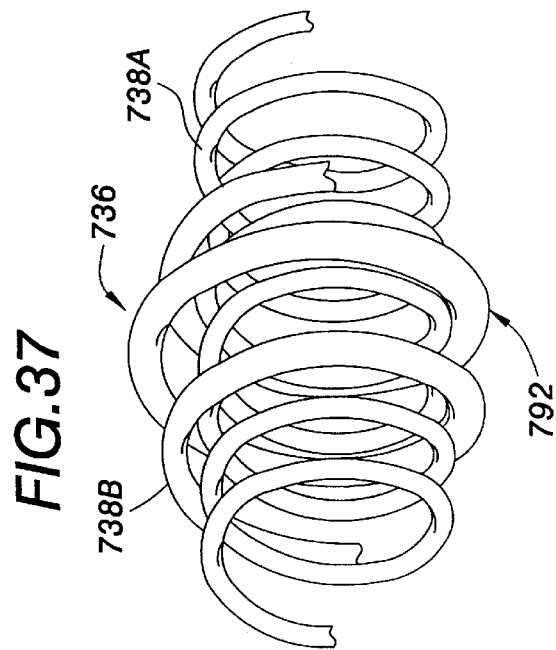
FIG.38
FIG.37

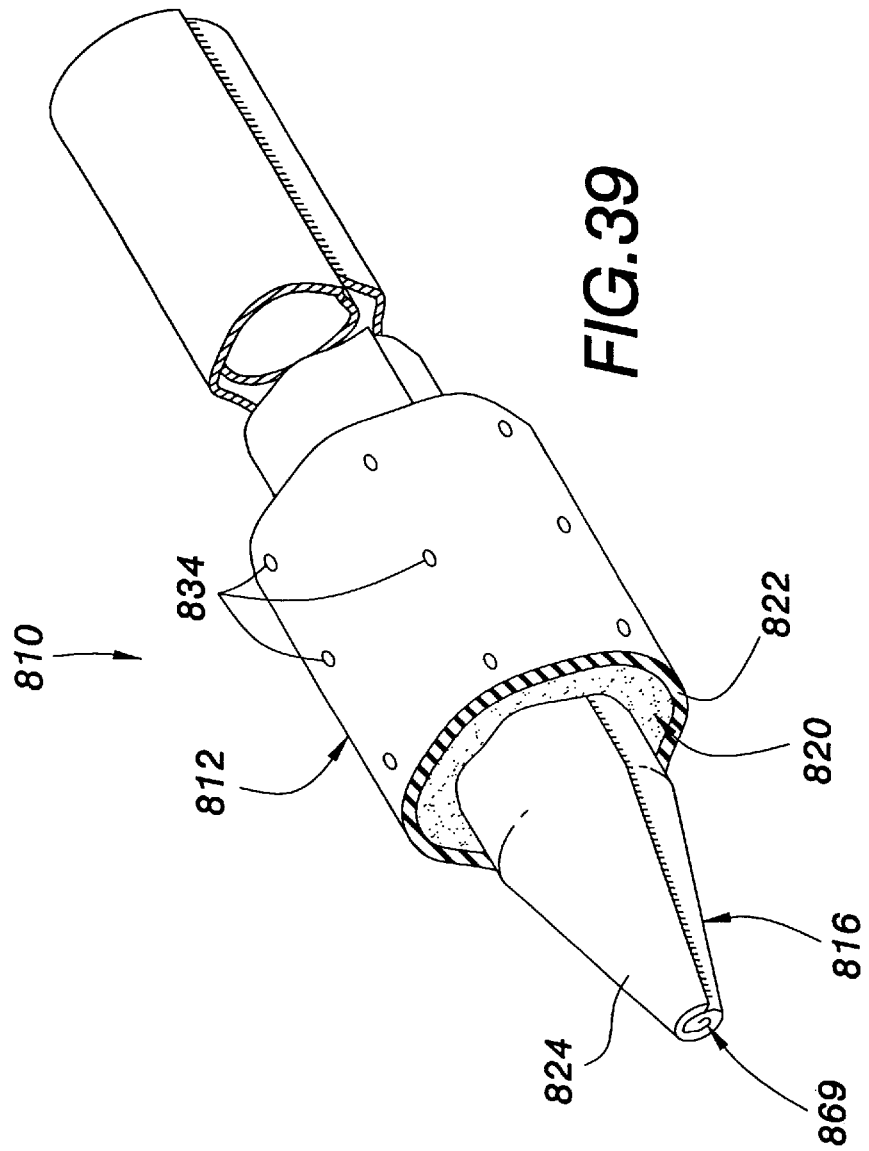

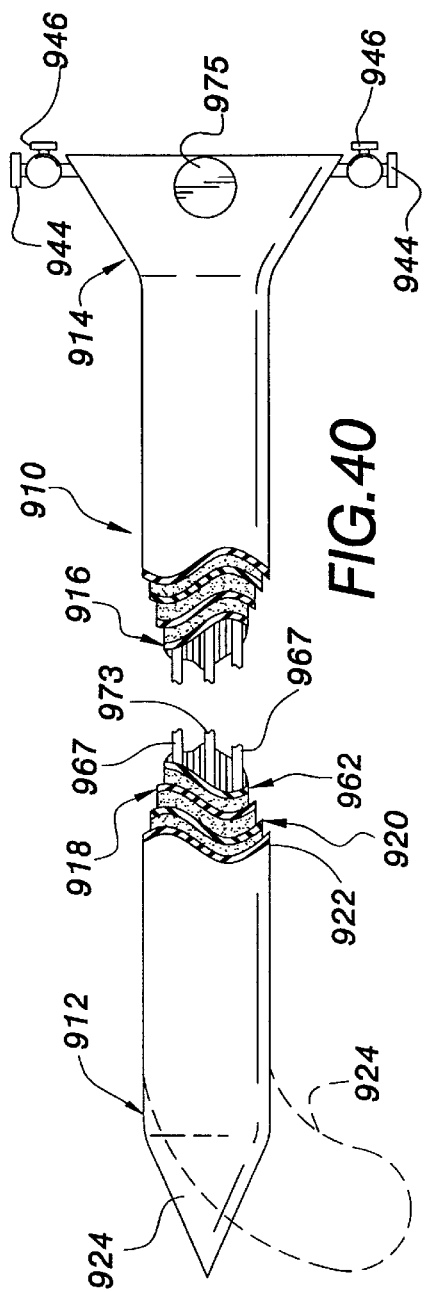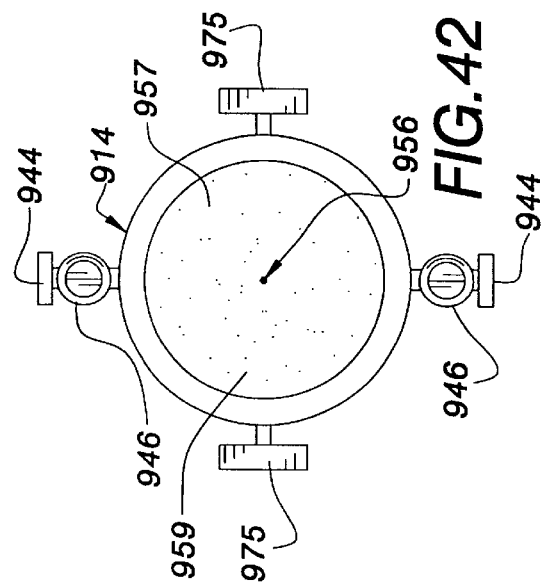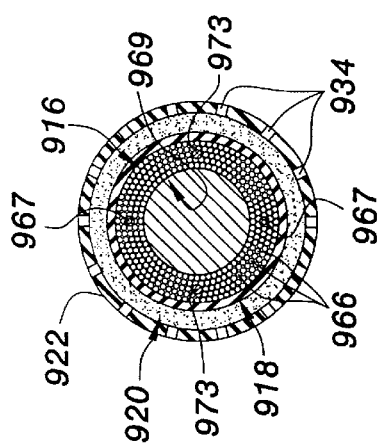

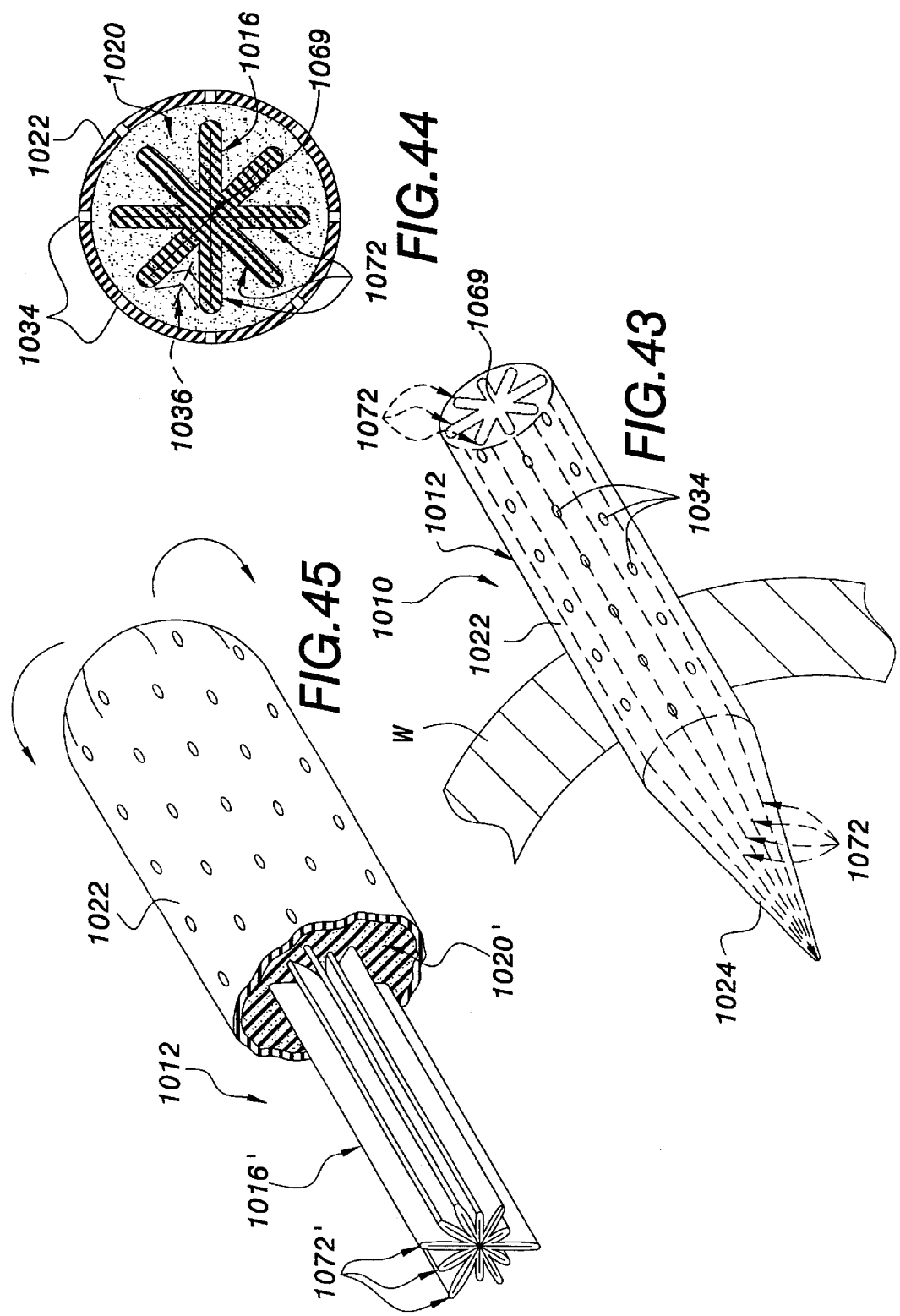

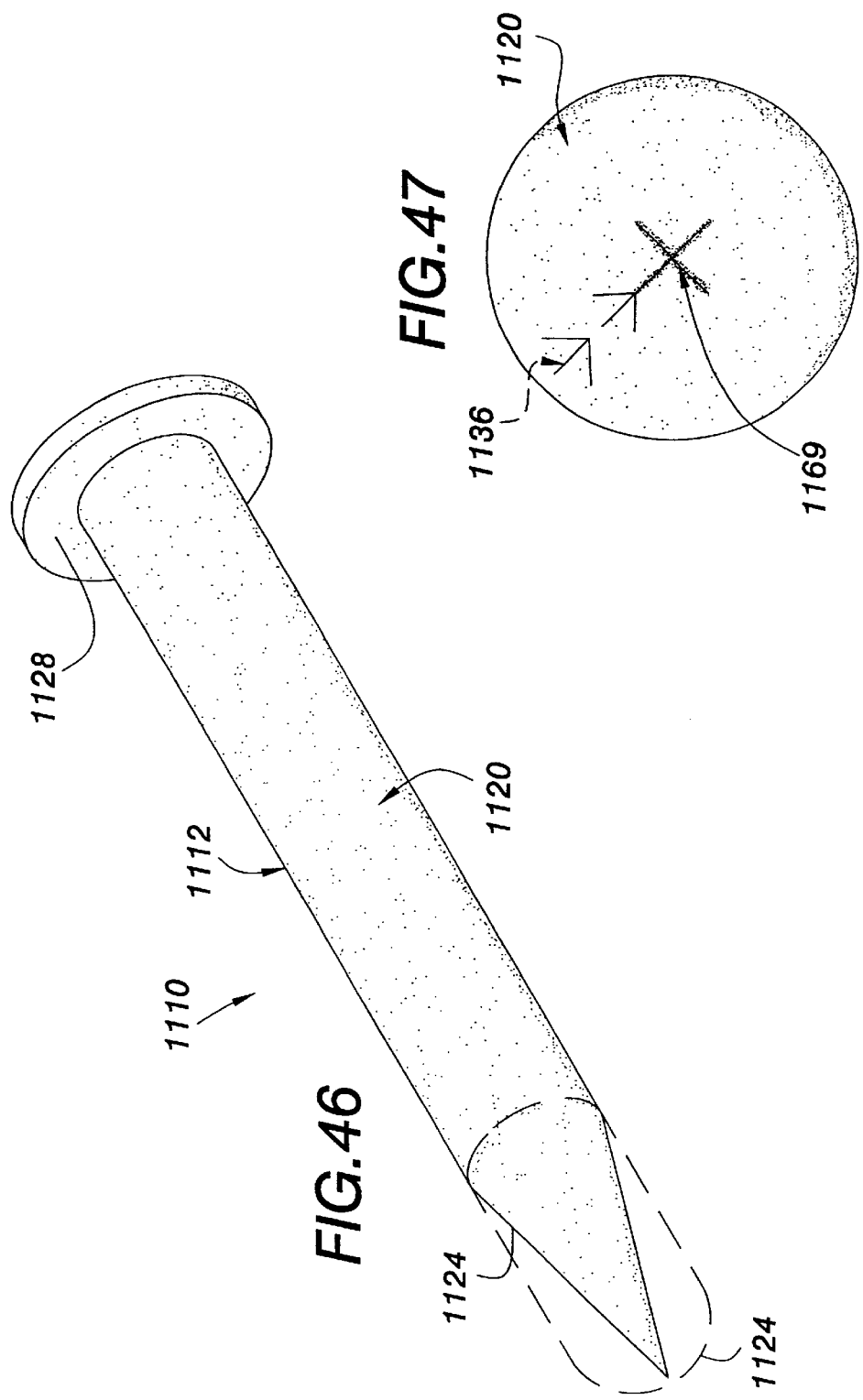

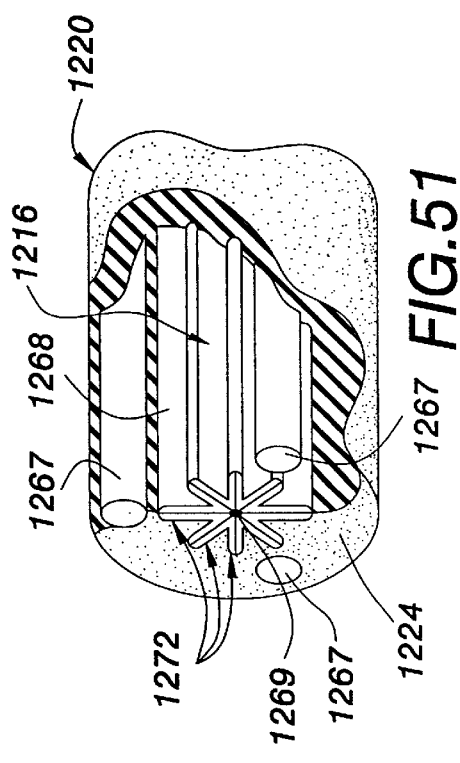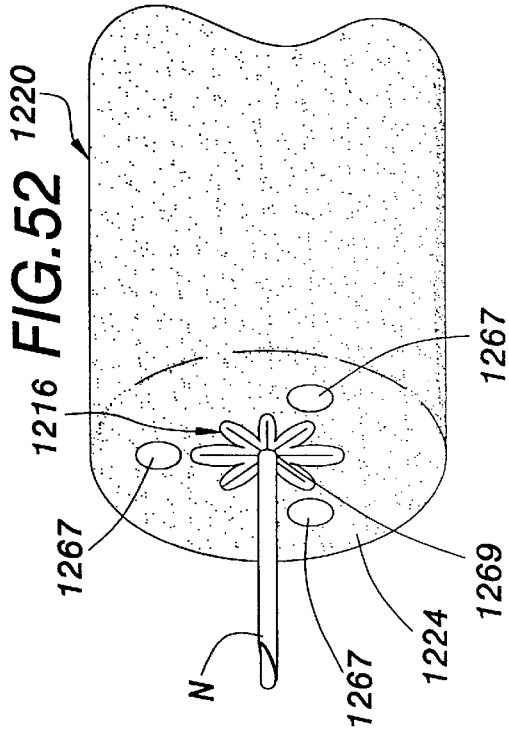

EXPANDABLE ENDOSCOPIC PORTAL AND METHODS THEREFOR

CROSS REFERENCE TO RELATED APPLICATIONS

This application is a divisional application of application Ser. No. 08/651,284 filed May 22, 1996, now U.S. Pat. No. 5,882,345.

BACKGROUND OF THE INVENTION

1. Field of the Invention

The present invention pertains to endoscopic portals for establishing communication with an internal site in a body cavity and, more particularly, to endoscopic portals having expandable cannulas providing a variable size lumen or passage through a cavity wall and to methods of establishing a passage through a cavity wall utilizing such endoscopic portals.

2. Discussion of the Related Art

In endoscopic procedures, a sleeve or cannula or other structure forming a passage is normally disposed in a body cavity wall such that a distal end of the cannula is positioned within the body cavity and a proximal end of the cannula is disposed externally of the body cavity with the lumen of the cannula providing a passage establishing communication with an internal site from externally of the body cavity. Typically, various instruments are introduced at the internal site through the passage of the cannula in order to perform diagnostic and/or surgical procedures, with the instruments many times having varying sizes in cross section. Since the passages of the cannulas are usually of fixed cross sectional size, it is necessary in a given procedure to utilize a cannula having a lumen large enough to accommodate the largest size instrument to be introduced in the body cavity. Accordingly, a puncture or opening is typically made through the cavity wall large enough to accommodate the cannula being used, and such opening may be larger than necessary when the instruments actually introduced are smaller in cross sectional size than the cross sectional size of the lumen. The sizes of punctures or openings in the cavity wall required to accommodate fixed size conventional cannulas in general necessitate performance of the endoscopic procedures at hospital sites. In order to reduce trauma and shorten recovery times for patients, to expand the use of non-hospital or outpatient sites for endoscopic procedures and to reduce costs, among other reasons, it would be desirable to begin an endoscopic operative procedure with as small a cannula as possible to minimize the size of the puncture or opening and to thereafter expand the cannula to non-traumatically stretch or dilate the puncture or opening to accommodate larger size instruments and/or anatomical specimens, such as organs, to be introduced in and/or withdrawn from the body. However, with endoscopic portals having fixed size cannulas, non-traumatic dilatation of the puncture or opening is not possible. Another disadvantage of presently utilized endoscopic portals is that the cannulas are not self-penetrating but require a separate penetrating member or obturator for penetrating the cavity wall.

It is important in endoscopic procedures to prevent undesired fluid flow to and from the internal site; and, accordingly, the endoscopic portals must be sealed prior to and subsequent to the introduction of instruments and while the instruments are in place. In particular, fluids such as gaseous phase carbon dioxide or nitrous oxide are normally introduced in the body for insufflation as part of the endoscopic procedure, and the escape of such gases through the endoscopic portal should be prevented. With fixed size cannulas, the size of instruments that can be introduced through the lumen is limited since instruments having a cross sectional size larger than the fixed cross sectional size of the lumen cannot be fit through the lumen; and, when instruments smaller in cross sectional size than the fixed cross sectional size of the lumen are introduced, a seal is not formed with the introduced instruments. Since the cross sectional size of the lumen must be large enough to accommodate the largest size instrument to be introduced in a procedure, there is a gap between the cannula and smaller size instruments introduced therethrough through which fluid can escape. Many endoscopic portals have valves to prevent leakage of fluid, such valves including one or more valve passages typically of fixed cross sectional sizes. The sizes of instruments that can be introduced in the valve passages is limited since fluids can escape past instruments having cross sectional sizes that do not correspond to the fixed cross sectional sizes of the valve passages. Universal seals having variable size passages for receiving and sealingly engaging instruments of various sizes have been proposed for endoscopic portals. Many of the universal seals proposed for endoscopic portals have various drawbacks including structural and functional complexity, the need for a separate seal housing, adding to the overall length of the endoscopic portals, and failing to provide adequate support for introduced instruments.

It is also desirable in endoscopic procedures that the cannula be stabilized relative to the cavity wall to prevent backing out of the cannula from the body cavity. Although stabilizers for endoscopic pertals have been proposed, most present various drawbacks due to their structural and operational complexity. In addition, conventional stabilizers typically do not afford stabilization relative to a primary cavity as well as a secondary cavity disposed in the primary cavity as would be desirable for cavity in a cavity procedures.

SUMMARY OF THE INVENTION

Accordingly, it is a primary object of the present invention to overcome the aforementioned disadvantages of prior art endoscopic portals by forming a cannula of an endoscopic portal as an absorbent member having a distal end for being disposed in a body cavity and a proximal end for being disposed externally of the body cavity with the absorbent member being rigid in a dry state to facilitate passage through a cavity wall and being soft in a wet state to define a variable size passage therethrough for receiving instruments of various cross sectional sizes in sealing relation.

Another object of the present invention is to provide an absorbent member that functions as an obturator for penetrating an anatomical cavity wall in a dry state and functions as a cannula providing a variable size passage through the cavity wall for receiving instruments of various sizes in a wet state.

A further object of the present invention is to utilize longitudinal expansion of an absorbent member in a wet state to shield a distal end of an instrument received in a cannula of an endoscopic portal.

Yet another object of the present invention is to provide a cannula with a safety shield held in a retracted position by an absorbent member in a dry state and released for movement to an extended position when the absorbent member is in a wet state.

An additional object of the present invention is to stabilize a cannula of an endoscopic portal relative to a body cavity wall utilizing an absorbent member that expands radially when hydrated with fluid to form a protuberance along the cannula.

Yet another object of the present invention is to form a cannula of an endoscopic portal as an absorbent member having a liner therein, the absorbent member being rigid in a dry state to facilitate passage through a cavity wall and being soft in a wet state with the liner providing a variable size passage through the absorbent member for receiving instruments in sealing relation in the dry state.

It is also an object of the present invention to create a seal between a cannula and a cavity wall through which the cannula extends by utilizing an absorbent member disposed along the thickness of the cavity wall and capable of expanding diametrically when hydrated with fluid to form a seal along the thickness of the cavity wall.

A still further object of the present invention is to provide a liner in an endoscopic portal having a cannula formed of an absorbent member to provide a variable size passage through the endoscopic portal for receiving instruments in sealing relation when the absorbent member is in a rigid dry state and in a soft wet state.

An additional object of the present invention is to position a cannula to extend through an opening in a cavity wall and to dilate the opening via expansion of an absorbent member of the cannula.

Some of the advantages of the present invention are that the cannula can assume a predetermined external configuration due to predetermined expansion of the absorbent member, the overall size and length of the endoscopic portal can be greatly minimized since a housing or head is not necessary, the cannula can be cut or trimmed to a desired length prior to use, the cannula can be used to clean an area within the body cavity and/or to collect or remove anatomical specimens from the body cavity, the absorbent member can be impregnated with agents useful in the procedure being performed, various substances can be supplied via the absorbent member, anesthetic can be delivered via the absorbent member such that more procedures can be performed endoscopically under local anesthesia, the absorbent member can be used to apply pressure to control bleeding, various coatings can be applied to the cannula to control porosity, frictional characteristics and/or to protect the friable material of the absorbent member, the cannula can be stabilized automatically in response to absorption of body fluids by the absorbent member, the absorbent member can be hydrated passively and/or actively via forced hydration, and the endoscopic portals can be inexpensively manufactured for single patient use.

These and other objects, advantages and benefits are realized with the present invention as characterized in an endoscopic portal comprising a cannula including an elongate absorbent member for being introduced through a body cavity wall and having a distal end for positioning in the body cavity, a proximal end for positioning externally of the body cavity and a lumen between the distal and proximal ends. The absorbent member has a dry state prior to introduction through the body cavity wall and a wet state when supplied with fluid upon introduction in the body. The absorbent member is rigid in the dry state and is soft and flexible in the wet state. According to one embodiment, a liner is disposed in the lumen of the absorbent member to define a variable size passage for receiving instruments of various sizes in sealing relation. The liner has a normal closed or initial position wherein the variable size passage has a first cross-sectional size and is moved to an open position by an instrument introduced in the variable size passage to enlarge the variable size passage to a second cross-sectional size to accommodate the introduced instrument. The liner can include various structure or coatings including a stretchable or non-stretchable membrane, a rolled spiral member, a plurality of flexible wires or rods and a universal seal. The universal seal includes a compressible member encapsulated in a membrane having an inner membrane section defining the variable size passage. The inner membrane section can be pleated or non-pleated, and a spine can be provided in the universal seal to bias the universal seal to the closed position. According to another embodiment, the lumen of the absorbent member itself defines a variable size passage in the wet state for receiving instruments of various sizes in sealing relation. The wet absorbent member maintains the first cross-sectional size of the variable size passage, allows the variable size passage to be enlarged to sealingly receive an instrument and causes the variable size passage to return to the first cross sectional size upon withdrawal of the instrument. When supplied with fluid to obtain the wet state, the absorbent member is expandable radially from its cross sectional size in the dry state to sealingly engage the body cavity wall along the thickness of the body cavity wall. The absorbent member in the wet state can form one or more protuberances for stabilizing the cannula relative to the cavity wall. The absorbent member can expand longitudinally in the wet state to perform a shielding function. Various spine members can be provided in the absorbent member for obtaining a predetermined external configuration for the absorbent member in the wet state, for supplying substances to the absorbent member to obtain the wet state, for evacuating fluid from the absorbent member to facilitate withdrawal from the body, for supplying fluid to the body cavity and/or for evacuating substances from the body cavity. The distal end of the absorbent member can be configured to penetrate the body cavity wall allowing the cannula to be utilized as an obturator in the dry state; and, the distal end becomes soft and blunt in the wet state upon entry in the body cavity. The cannula can include a shield maintained in a retracted position by the absorbent member in the dry state and released for movement to an extended position when the absorbent member is in the wet state. The cannula can include a passage defining member disposed in the include a passage defining member disposed in the lumen of the absorbent member, and the liner can be disposed in the passage defining member. A membrane can be disposed over the absorbent member, and the membrane can be provided with perforations through which the absorbent member can absorb body fluid to obtain the wet state. The absorbent member can be hydrated actively via fluid supplied from external of the body, such as via the spine members or one or more channels in the absorbent member.

A method of establishing a passage through a body cavity wall according to the present invention comprises the steps of introducing an elongate absorbent member in an opening in the cavity wall with the absorbent member in a dry state, positioning a distal end of the absorbent member in the body cavity and a proximal end of the absorbent member externally of the body cavity with the absorbent member extending longitudinally through the opening in the cavity wall, and hydrating the absorbent member to place the absorbent member in a wet state causing the absorbent member to expand radially within the opening.

Other objects and advantages of the present invention will become apparent from the following description of the preferred embodiments taken in conjunction with the accompanying drawings wherein identical reference numbers indicate identical parts or parts providing identical function.

BRIEF DESCRIPTION OF THE DRAWINGS

FIG. 3 is a broken perspective view of the cannula in the expanded configuration with the absorbent member in the wet state.

FIG. 4 is a broken, side sectional view of the endoscopic portal showing the cannula in the expanded configuration with the spine of the absorbent member in an extended configuration.

FIG. 7 is a sectional view of the endoscopic portal of FIG. 1 showing the cannula in the non-expanded configuration showing the liner in a closed or initial position.

FIG. 8 is an exploded, broken perspective view of the liner.

FIG. 9 is a broken perspective view of a spine member for the liner.

FIG. 10 is a broken perspective view of a modification of a spine member for the liner.

FIG. 11 is a broken side view, partly in section, of the endoscopic portal of FIG. 1 showing the liner in an open or second position receiving a trocar through the cannula.

FIG. 12 is a sectional view of the endoscopic portal taken along line 11—11 of FIG. 11.

FIG. 14 is a broken side view, partly in section, of the endoscopic portal showing the cannula in the expanded configuration extending through the cavity wall with the liner in a further open position to receive an instrument.

FIG. 15 is a sectional view of the endoscopic portal Showing the variable size passage of the liner enlarged with a tubular expander to withdraw a body specimen therethrough.

FIG. 16 is a broken, side sectional view of the cannula without a spine for the absorbent member.

FIG. 18 is a broken, side sectional view of a modification of an endoscopic portal according to the present invention showing the cannula in the expanded configuration.

FIG. 19 is a sectional view of the endoscopic portal of FIG. 18 showing the cannula in the non-expandable configuration with the liner in the initial position.

FIG. 20 is a broken perspective view of the inner membrane of the liner of the endoscopic portal of FIG. 18.

FIG. 21 is a broken perspective view of a spine member for the liner of the endoscopic portal of FIG. 18.

FIG. 22 is a broken perspective view of a modification of the inner membrane of the liner.

FIG. 23 is a broken perspective view of a modification of a spine member for use in the endoscopic portals according to the present invention showing the spine member in the normal extended configuration.

FIG. 24 is a broken perspective view of another modification of a spine member for use in the endoscopic portals according to the present invention showing the spine member in the normal extended configuration.

FIG. 25 is a broken perspective view of a further modification of a spine member for use in the endoscopic portals according to the present invention showing the spine member in the normal extended configuration.

FIG. 26 is a broken, side sectional view of a further modification of an endoscopic portal according to the present invention showing the cannula in the non-expanded configuration.

FIG. 27 is a side sectional view of the endoscopic portal of FIG. 26 showing the cannula in the expanded configuration extending through a body cavity wall.

FIG. 28 is a broken, side sectional view of a further modification of an endoscopic portal according to the present invention showing the cannula in the non-expanded configuration with a safety shield of the cannula a retracted position.

FIG. 29 is a broken, side sectional view of the endoscopic portal of FIG. 28 showing the liner therefor in an open position receiving a trocar.

FIG. 30 is a broken side view, partly in section, of the endoscopic portal of FIG. 28 showing passage of the cannula through a body cavity wall with the safety shield in the retracted position.

FIG. 31 is a broken side view, partly in section, of the endoscopic portal of FIG. 28 showing the cannula in the expanded configuration with the safety shield in the extended position.

FIG. 32 is a broken, side sectional view of the endoscopic portal of FIG. 31 showing the trocar withdrawn from the endoscopic portal.

FIG. 33 is a partially broken side view of another modification of an endoscopic portal according to the present invention showing the cannula in the non-expanded configuration.

FIG. 34 is a broken perspective view of a spine member for the endoscopic portal of FIG. 33 showing the spine member in the extended configuration.

FIG. 35 is a sectional view of the cannula of FIG. 33.

FIG. 36 is a partially broken side view of the endoscopic portal of FIG. 33 showing the cannula in the expanded configuration extending through a body cavity wall.

FIG. 37 is a broken perspective view of a modification of the spine member for the endoscopic portal of FIG. 33 showing the spine member in the extended configuration.

FIG. 38 is a broken perspective view of a further modification of the spine member for the endoscopic portal of FIG. 33 showing the spine member in the extended configuration.

FIG. 39 is a broken perspective view of an additional modification of an endoscopic portal according to the present invention showing the cannula in the non-expanded configuration.

FIG. 40 is a broken side view of a further modification of an endoscopic portal according to the present invention showing the cannula in the non-expanded configuration.

FIG. 41 is a sectional view of the cannula of FIG. 40 receiving an instrument therethrough.

FIG. 42 is an end view of the endoscopic portal of FIG. 40.

FIG. 43 is a perspective view of an additional modification of an endoscopic portal according to the present invention showing the cannula extending through a body cavity wall.

FIG. 44 is a sectional view of the cannula of FIG. 43.

FIG. 45 is a broken perspective view of a modification of the cannula of the endoscopic portal of FIG. 43.

FIG. 46 is a perspective view of another modification of an endoscopic portal according to the present invention showing the cannula in the non-expanded configuration.

FIG. 47 is an end view of the cannula of FIG. 46.

FIG. 51 is a broken perspective view of the distal end of the cannula of the endoscopic portal of FIG. 48 showing the cannula in the non-expanded configuration.

FIG. 52 is a broken perspective view of the distal end of the cannula of the endoscopic portal of FIG. 48 showing the cannula in the expanded configuration with a Verress needle introduced therethrough.

DESCRIPTION OF THE PREFERRED EMBODIMENTS

Figure 1:
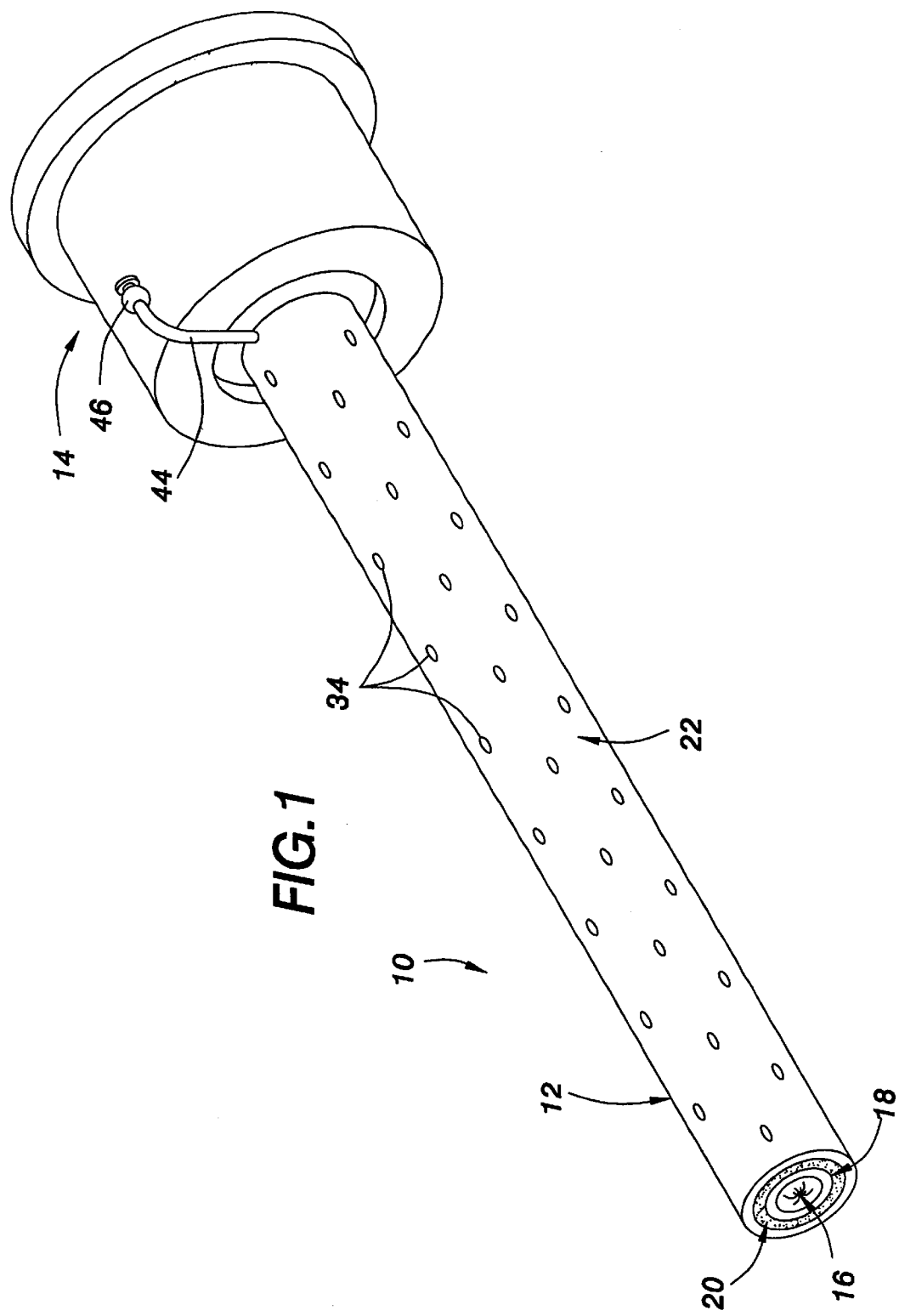
FIG. 1 is a perspective view of an endoscopic portal according to the present invention.
Figure 2:
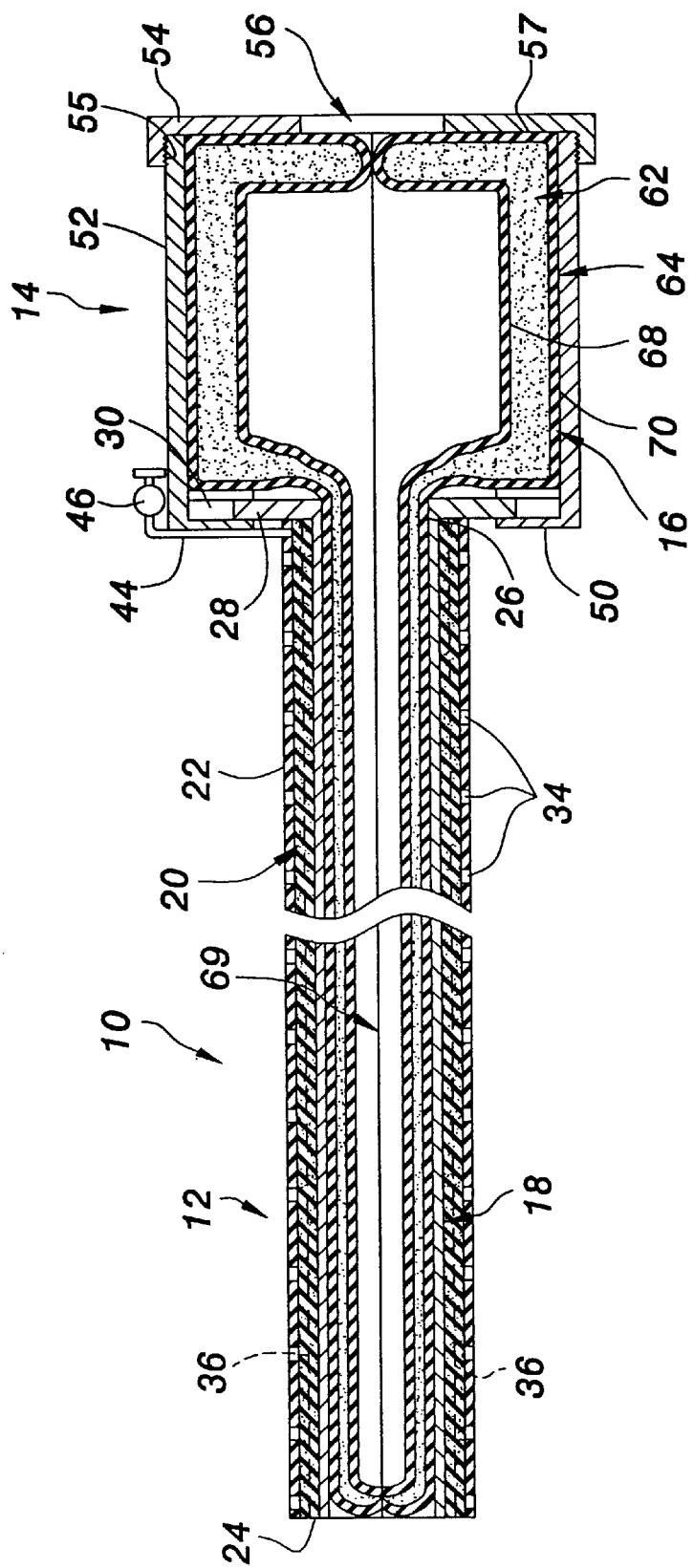
FIG. 2 is a broken, side sectional view of the endoscopic portal showing the cannula in the non-expanded configuration with the absorbent member in the dry state.

An expandable endoscopic portal 10 according to the present invention is illustrated in FIGS. 1 and 2 and includes an elongate cannula 12, a housing or head 14 at a proximal end of cannula 12 and a liner 16 disposed in cannula 12 and housing 14. Cannula 12 includes a hollow cylindrical or tubular passage defining member or sleeve 18 which, for example, can take the form of a portal sleeve or other structure providing a passage through a cavity wall, an absorbent member 20 concentrically disposed over sleeve 18 and a membrane 22 concentrically disposed over absorbent member 20. Sleeve 18 has an open distal end 24 for being disposed in a body cavity, an open proximal end 26 for being disposed externally of the body cavity and a lumen or passage between the distal and proximal ends. Sleeve 18 terminates proximally at a transverse flange 28 received in a recess 30 in a forward wall of housing 14. A longitudinal slit 32, shown in FIG. 3, is provided in the wall of sleeve 18 extending the entire length thereof to permit expansion of sleeve 18 diametrically or in a direction transverse to a longitudinal axis of cannula 12 to increase or enlarge the cross sectional size of the lumen. Sleeve 18 is disposed in a normal, non-expanded position wherein the slit 32 is closed or substantially closed with the slit edges in contact with or close to one another, and the slit 32 is opened such that the slit edges are moved away from one another when the sleeve 18 is expanded diametrically or transversely in an expanded position by an instrument or object introduced through seal 16 as explained further below. To permit diametric transverse expansion of sleeve 18, recess 30 is larger than flange 28 diametrically or in the transverse direction when the sleeve 18 is in the normal non-expanded position to provide a space into which the flange 28 is moved when the sleeve 18 is moved to the expanded position. Sleeve 18 can be made of any suitable medical grade material including various rigid, semi-rigid, flexible, bendable or stretchable materials such as metals, plastic and rubbers capable of expanding diametrically or transversely due to the resilience or flexibility of the materials themselves and/or due to structure such as hinges, pivots or joints provided in or on the sleeve 18. Where the sleeve is made of a relatively soft material, such as plastic or rubber, the sleeve 18 can be cut or trimmed to a desired length prior to use in accordance with a procedure to be performed utilizing the endoscopic portal. Fabricating the sleeve of a soft material has the additional advantage of minimizing trauma or damage to tissue during use.

Absorbent member 20 has a compressed, dry state prior to absorbing fluids and an expanded, wet state after absorbing fluids. Absorbent member 20 can be made of any type of medical grade absorbent material capable of absorbing fluids and expanding outwardly, diametrically, radially or in a direction transverse to a longitudinal axis of cannula 12, from its size in the dry state. The absorbent member can be designed for transverse or diametric expansion alone, such as by being adhesively attached to sleeve 18; however, the absorbent member can also be designed to expand longitudinally as well as transversely. The absorbent member 20 is compressed and rigid or stiff in the dry state to facilitate passage through a cavity wall. When compressed and dry, the absorbent member 20 has properties, i.e. density, flexural modulus, hardness and tensile strength, similar to wood. The absorbent member 20 becomes soft and pliant, malleable, resilient or flexible in the expanded, wet state after absorbing fluids and behaves like a typical sponge. It is desirable that the absorbent member 20 absorb fluids and expand rapidly. Open cell sponge-like materials are preferred for the absorbent member 20, and exemplary materials include compressed cellulose sponge, natural sponge, synthetic sponge made of a reaction product of polyvinyl alcohol and formaldehyde, hydrophilic cross-linked polyurethane foam and compacted gauze or cotton. The absorbent member 20 is preferably compressible in the wet state to facilitate withdrawal of the cannula 12 from the body. As shown in FIG. 2, the absorbent member 20 is tubular and extends the entire length of sleeve 18 distally of housing 14. The absorbent member 20 is of uniform, minimal thickness in the compressed, dry state so as not to add significantly to the external diameter or cross sectional size of the sleeve 18. The absorbent material 20 can be attached to sleeve 18 and/or to membrane 22, such as adhesively, or the absorbent member 20 can be unattached and held between membrane 22 and sleeve 18. Membrane 22 includes a thin layer of stretchable or elastic material such as Tecoflex, Teflon, Goretex or rubber, for example, disposed over absorbent member 20. Membrane 22 can be made as a tubular or hollow structure concentrically disposed over absorbent member 20, and the membrane 22 can be slightly stretched or can be relaxed when the absorbent member 20 is in the dry state. Another way in which membrane 22 can be fabricated, by way of example, is as a sheet of stretchable material wrapped around absorbent member 20 with end edges of the sheet sealed together. A plurality of small holes or perforations 34 are formed in membrane 22 to permit body fluids to be absorbed by absorbent member 20 as explained below. Absorbent member 20 and membrane 22 are distally coterminal with sleeve 18 such that distal ends of absorbent member 20 and membrane 22, respectively, are aligned with the distal end 24 of sleeve 18, and together define a distal end 24 for cannula 12. Membrane 22 does not extend over or cover the thickness of the absorbent member 20 at the distal end 24 to facilitate absorption of body fluids by absorbent member 20. It should be appreciated, however, that the membrane 22 can extend over the thickness of the absorbent member 20 at the distal end 24. Membrane 22 terminates proximally, externally adjacent housing 14; however, the membrane can extend into the housing 14. The membrane 22 can be attached to the sleeve distal end 24 and/or to the sleeve proximal end 26 or to the housing 14.

As best shown in FIGS. 3 and 4, a spine is disposed between sleeve 18 and membrane 22 and includes a plurality of spine members 36 disposed around the longitudinal axis of cannula 12. Four spine members 36 are shown in FIG. 3 by way of example at 90° spaced locations about the cannula longitudinal axis. Each spine member 36 is formed of a straight, elongate tubular trunk 38 parallel with the cannula longitudinal axis and straight tubular branches 40 and curved tubular branches 42 extending from trunk 38. The spine members 36 extend the entire or substantially the entire length of cannula 12; and, where the spine members are wholly or partially tubular, one or more of the spine members 36 can be provided with holes or openings 48, as shown in FIG. 4. Distal ends of the spine members terminate at the distal end 24 to communicate with the body cavity; however, the spine members can be closed at their distal ends. As shown in FIG. 2, a proximal end of one or more spine members is connected with one or more fluid conduits, fittings or ports, such as port 44 disposed adjacent housing 14. Port 44, which is flexible, communicates with a valve 46, such as a stop cock, and is connectible with a source of fluid, such as insufflation gas, for introducing fluid in the body cavity via the port 44 and the associated tubular spine member 36 where the associated spine member is provided without holes 48. Where the spine member associated with port 44 is provided with holes 48, fluid can be supplied to the absorbent member 20 via the port 44. In the same manner, one or more spine members 36 can be connected with an evacuation or suction port connectible with a source of suction or vacuum for evacuating or aspirating substances, such as fluids and tissue, from the body cavity where the associated spine member is provided without holes 48; and, where the associated spine member is provided with holes 48, fluid can be aspirated from the absorbent member 20 through the associated spine member. Accordingly, in addition or alternative to passive hydration of the absorbent member 20 via absorption of body fluids, the absorbent member 20 can be actively hydrated via fluid supplied to the absorbent member 20 from externally of the body cavity. Where the absorbent member is actively hydrated, the membrane 22 can be provided without perforations 34. It should be appreciated that a combination of spine members can be provided in absorbent member 20 to define supply and/or evacuation channels through the absorbent member for performing different functions, i.e. forced hydration of absorbent member 20, evacuation of fluid from absorbent member 20, supply of substances including medicaments and therapeutic agents, to the body cavity and evacuation of substances from the body cavity.

Each spine member 36 has a normal, extended configuration shown in FIGS. 3 and 4 wherein branches 40 extend from trunk 38 at an acute angle to the distal direction, the branches 40 having first ends flexibly, resiliently or pivotally mounted to trunk 38 and having second, free or unattached ends. Distally and proximally of curved branches 42, the straight branches 40 are arranged in pairs along trunk 38 with one branch 40A of each pair extending from trunk 38 in the direction of membrane 22 and the other branch 40B of each pair extending from trunk 38 in the direction of sleeve 18 with the branches 40A and 40B of each pair being spaced from one another longitudinally along trunk 38. Branches 40B extend along the portion of the length of trunk 38 corresponding to curved branches 42 while branches 40A do not. Branches 42 curve outwardly from trunk 38 in the normal, extended configuration and have first ends flexibly, resiliently or pivotally mounted to trunk 38 and second, free or unattached ends. Three branches of similar curvature and increasing length are provided on each spine member 36 with the branches being arranged in nesting fashion from shortest to longest with the shortest branch disposed closest to trunk 38, the longest branch disposed furthest away from trunk 38 and the next longest branch disposed between the longest and shortest branches. Branches 42 of the spine members 36 disposed at 1800 spaced locations are coplanar with one another, with trunks 38 and with the cannula longitudinal axis, and the branches 42 curve outwardly from trunks 38 in a direction away from the cannula longitudinal axis. Accordingly, the branches 42 and trunks 38 of the first pair of spine members disposed at 180° spaced locations are disposed in a first plane containing the cannula longitudinal axis, and the branches 42 and trunks 38 of the second pair of spine members disposed at 180° spaced locations are disposed in a second plane containing the cannula longitudinal axis and bisecting the first plane. Branches 42 are made of a resilient, flexible or spring material allowing branches 42 to be compressed or flattened toward trunks 38.

Figure 5:
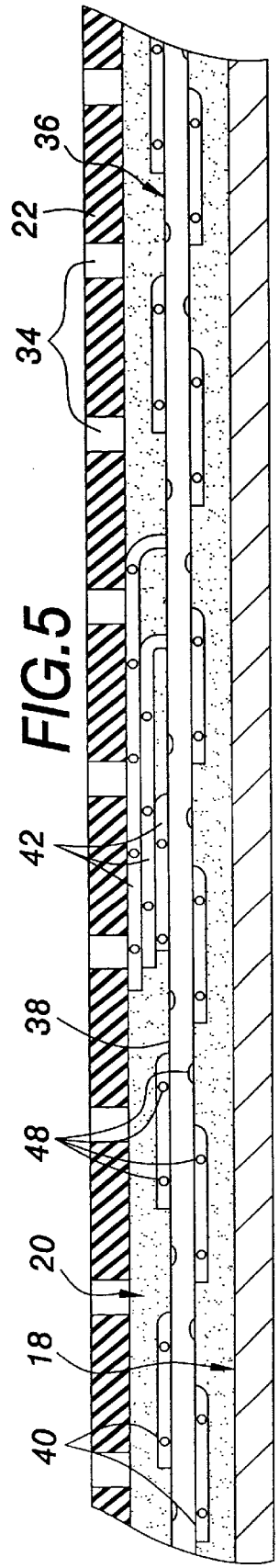
FIG. 5 is a broken, fragmentary, side sectional view of the cannula in the non-expanded configuration with the spine of the absorbent member in a contracted configuration.

The spine members 36 are movable from the normal extended configuration to a constrained, collapsed or contracted configuration wherein branches 40 and 42 are disposed close to or in contact with trunks 38 in substantial alignment therewith as shown in FIG. 5. In the contracted configuration, branches 40 are pivoted about their first ends toward the corresponding trunk 38 such that the branches 40 lie flat against trunk 38. Branches 42 are pivoted about their first ends or are flattened to lie parallel or substantially parallel with and close to the corresponding trunk 38 in overlapping fashion. Accordingly, in the contracted configuration, the spine members 36 fit within the thickness of the absorbent member 20 in the dry state. The absorbent member 20 is compressed around the spine members 36 in the dry state and, due to the stiffness and rigidity of the absorbent member in the dry state, maintains or constrains the spine members 36 in the contracted configuration. The spine members 36 have resilience and/or shape memory, such as by being made from a material having resilient spring-like properties, causing the spine members to return automatically to the normal, extended configuration when the absorbent material 20 becomes soft and pliable in the wet state. The spine members 36 are shown disposed within or embedded in the layer of absorbent member 20; however, the spine members can be disposed externally of the absorbent member partly or entirely, such as being interposed between the absorbent member 20 and the membrane 22 or between the absorbent member 20 and the sleeve 18. Any number of spine members 36 can be provided to obtain a desired external configuration for cannula 12 in the wet state. The spine can include individual, separate spine members as shown for endoscopic portal 10, or the spine can be designed as an integral, unitary structure with interconnected spine members. The spine members can be either tubular or solid or the branches can be solid with only the trunks tubular.

The spine members 36 can be formed of any suitable material having resilience and/or shape memory and having a normal, non-straight or extended predetermined configuration designed for a particular procedure. During manufacture, the spine members are straightened and the absorbent member 20 is compressed around the spine members such that the dry, stiff condition of member 20 maintains the spine members in the contracted configuration. If necessary, the absorbent member can be attached to the spine members, for example with adhesive, Once fluid has been absorbed by absorbent member 20, the spine members 36 return to the normal, extended configuration. It may be desirable that the absorbent member 20 be disposed around the spine members 36 to prevent contact of the spine members 36 with the membrane 22.

The materials, structure and construction of the absorbent member and the spine therefor can be like those disclosed in applicant's prior applications Ser. No. 08/130,484 filed Oct. 1, 1993 and Ser. No. 08/487,215 filed Jun. 7, 1995 and in applicant's prior U.S. Pat. Nos. 5,074,840, 4,374,261, 5,392, 787 and 5,439,457 incorporated herein by reference.

Housing 14 can be made of any suitable materials such as plastics and metals and can have any desirable configuration to facilitate grasping including a cylindrical configuration as shown in FIG. 1. As shown in FIG. 2, housing 14 includes transverse forward wall 50 having recess 30 therein receiving flange 28, a cylindrical body 52 extending proximally from forward wall 50 and an end cap 54 removably mounted on an open proximal end of cylindrical body 52. End cap 54 can be removably mounted on cylindrical body 52 in many various ways including a threaded connection as shown at 55 in FIG. 2. End cap 54 defines a transverse rearward wall of housing 14, the rearward wall 54 being parallel to forward wall 50 and having an opening 56 therein longitudinally or axially aligned with the lumen of sleeve 18. Opening 56 is of a size large enough to accommodate the cross sectional size of the largest instrument or object to be introduced and/or withdrawn through the endoscopic portal 10 for a specific procedure allowing the largest size instrument or object as well as smaller size instruments or objects to pass therethrough. Since the end cap 54 is removable from cylindrical body 52, the end cap 54 can be removed and replaced with another, different end cap having a larger opening to accommodate larger size instruments or objects, or the end cap 54 can be replaced with an end cap having an opening corresponding in size to the cross sectional size of a particular instrument.

Figure 6:
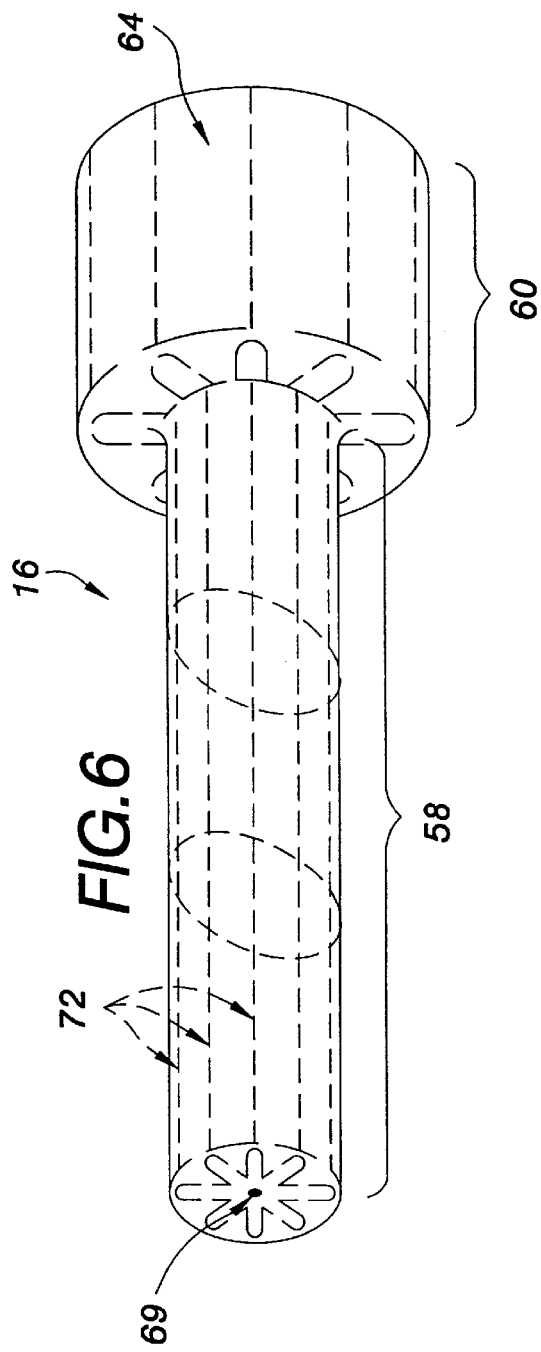
FIG. 6 is a perspective view of the liner for the endoscopic portal of FIG. 1.

As shown in FIG. 6, universal seal 16 includes a cannula portion 58 disposed within cannula 12 and a housing portion 60 disposed in the interior of housing 14. The cannula portion 58 has an external cross sectional size to fill the lumen of sleeve 18, and the housing portion 60 has an external cross sectional size, greater than the external cross sectional size of cannula portion 58, to fill the cross sectional interior of cylindrical body 52. The cannula portion 58 has a length to extend the entire or substantially the entire length of sleeve 18, and the housing portion 60 has a length to fill the interior of housing 14 longitudinally between forward wall 50 and rearward wall 54. As best shown in FIG. 7, seal is made up of a compressible member 62, a membrane 64 encapsulating compressible member 62 and a spine including a plurality of spine members 66 within compressible member 62. Membrane 64 includes an inner membrane section 68 disposed within a longitudinal passage of the compressible member and defining a variable size passage 69 and an outer membrane section 70 disposed around inner membrane section 68 and compressible member 62. The inner and outer membrane sections are connected to one another to define a closed or sealed envelope containing compressible member 62, which is disposed between the inner membrane section 68 and the outer membrane section 70. As shown in FIG. 7 and in FIG. 8, which shows the inner membrane section 68 without the outer membrane section, inner membrane section 68 is pleated or folded about a longitudinal axis of seal 16, coaxial with the cannula longitudinal axis, to define a plurality of interconnected, radial pleats or folds 72 about variable size passage 69. Inner membrane section 68 has a sphincter configuration with each pleat 72 defined by two juxtaposed walls 74 extending radially to the longitudinal axis of seal 16, which is coincident with variable size passage 69, an outer bend 76 joining walls 74 to one another and an inner bend 78 for each wall 74, the inner bends 78 joining walls 74, respectively, to the walls of adjacent pleats, respectively. As shown in dotted lines in FIG. 6, pleats 72 extend lengthwise from a distal end of seal 16 to a proximal end thereof, with outer bends 76 extending longitudinally along absorbent member 20. Along the cannula portion 58, each pleat 72 extends a first radial distance from the longitudinal axis of seal 16; and along the housing portion 60, each pleat 72 extends a second radial distance, greater than the first radial distance, from the longitudinal axis of seal 16 such that the outer bends 76 are spaced inwardly the same distance from the outer membrane section 70 along the cannula portion and the housing portion. However, it should be appreciated that the distance that the pleats extend radially from the seal longitudinal axis can be the same along the cannula portion 58 and the housing portion 60 in which case the outer bends 76 will be spaced inwardly from the outer membrane section 70 a greater distance along the housing portion 60. The membrane 64 can be made of various medical grade materials as described for membrane 22. The outer membrane section 70 is stretchable; however, the inner membrane section 68 can be non-stretchable or stretchable. Preferably, at least the inner membrane section 68 is made of a slippery, tearing resistant or non-breakable material.

Compressible member 62 disposed within the envelope defined by membrane 64 comprises a body of compressible material filling the space between the inner membrane section 68 and the outer membrane section 70 and between adjacent pleats 72 such that the walls 74 of each pleat 72 are in contact with one another and the inner bends 78 are urged inwardly toward one another in the direction of the seal longitudinal axis. Compressible member 62 and/or spine members 66 biases the seal 16 to a normal closed or initial position wherein the inner bends are biased into contact with one another along variable size passage 69 such that the variable size passage 69 through seal 16 is normally closed or is of a first cross sectional size. Seal 16 fills sleeve 18 and housing 14 such that outer membrane section 70 is in contact with the internal surfaces of sleeve 18 and housing 14. The distal end of seal 16 is aligned with or adjacent the distal end 24 of sleeve 18, and a proximal end of seal 16 abuts end cap 54 with variable size passage 69 communicating with opening 56 of end cap 54. The body of compressible material can include various materials such as sponge, fluid, foam and gel, the compressible member 62 being made of compressible sponge.

FIG. 8 illustrates schematically one way of forming seal 16, only the inner membrane section 68 being shown. Compressible member 62, only a portion of which is shown, has a first cylindrical section, shown in FIG. 8, corresponding to cannula portion 58 and a second cylindrical section (not shown), larger in cross sectional size than the first cylindrical section, corresponding to housing portion 60. The first and second cylindrical sections can be integrally, unitarily formed. A recess 80 extends longitudinally through the compressible member 62 and has a multi-lobed configuration in cross section defining a radially extending recess lobe 82 for each pleat 72. Membrane 64 is disposed in recess 80 with each pleat 72 disposed in a corresponding recess lobe 82. A portion of membrane 64 extending externally from compressible member 62 is folded back over the compressible member 62 to form outer membrane section 70. The inner and outer membrane sections 68 and 70 are joined to one another at their ends, such as adhesively or via heat sealing or bonding. Spine members 66 are not shown in FIG. 8; however, it should be appreciated that the spine members 66 can be disposed within the compressible member 62 prior to assembly of compressible member 62 with membrane 64. The seal 16 can also be formed by various molding and extrusion processes.

Spine members 66, best illustrated in FIGS. 7 and 9, each include a straight trunk 84 and straight branches 86 extending angularly from trunk 84. Each trunk 84 includes an elongate planar strip of material of uniform thickness and having parallel outer and inner edges 88 and 90, respectively, extending the length of trunk 84. Each spine member 66 is arranged within compressible member 62 to be disposed between two adjacent pleats 72 with the trunk 84 thereof disposed in a plane radial to the seal longitudinal axis. Each trunk 84 is disposed mid-way between two adjacent pleats 72 with inner edge 90 disposed closer to the seal longitudinal axis than outer edge 88. The branches 86 include a pair of short branches 86A and a pair of long branches 86B extending angularly outwardly from trunk 84 toward the adjacent pleats 72. Branches 86A are angled symmetrically from opposite sides of trunk 84 and have first ends attached to trunk 84 at inner edge 90 with the branches 86A extending angularly outwardly from trunk 84 in the direction of outer edge 88 to terminate at unattached second ends. Branches 86B are angled symmetrically from opposite sides of trunk 84 and have first ends attached to trunk 84 between outer edge 88 and inner edge 90 with the branches 86B extending angularly outwardly from trunk 84 in the same direction as branches 86A such that the branches 86A and 86B disposed on the same side of trunk 84 are parallel with one another. Each branch 86 is made as an elongate, planar strip of material of uniform thickness joined along one edge to trunk 84 and extending the entire length thereof. Branches 86 are shown contacting membrane 64 in FIG. 7; however, the compressible member 62 will preferably be disposed around the spine members 66 such that no parts of the spine members 66 contact membrane 64. Spine members 66 add stiffness or rigidity to the compressible member 62 to maintain the normal closed position for seal 16. It should be appreciated, however, that where the compressible member 62 has sufficient rigidity, stiffness, or strength, a spine is not necessary. The spine members 66 can be disposed within the compressible member 62 in many various ways including being embedded in the compressible member, being disposed in preformed recesses of the compressible member and via molding and extrusion processes. If necessary, the spine members 66 can be attached, such as adhesively, to the compressible member. The spine members 66 extend the entire or substantially the entire length of the universal seal 16; and accordingly, each spine member extends longitudinally along both the cannula portion 58 and the housing portion 60 in which case the spine members can be bent or angled at the junction of the sleeve portion 58 with the housing portion 60. Alternatively, each spine member 66 can be discontinuous and made of separate, unattached segments. The spine members can be made of flexible, resilient materials having spring-like properties to bend, deform, buckle or "give" when the seal 16 is moved to an open position to accommodate an object introduced therethrough or the spine members can be made of rigid materials and merely pivoted, deflected or moved by an object introduced through seal 16 to accommodate the object in variable size passage 69. As shown in FIG. 10, the spine members 66 can be designed with each branch 86A being made up of individual branch segments 86A' longitudinally spaced from one another along the trunk 84 and with each branch 86B being made up of branch segments 86B' longitudinally spaced from one another along trunk 84 with the branch segments 86A' being staggered with respect to the branch segments 86B'. The liner can be in the form of the valve disclosed in applicant's prior U.S. Pat. Nos. 5,389,080, 5,429,609 and 5,441,486 incorporated herein by reference, which also discloses materials suitable for construction of seal 16.

Prior to use, absorbent member 20 is in the dry state with spine members 36 maintained in the contracted configuration. Sleeve 18 is in the normal non-expanded position with slit 32 closed. Accordingly, cannula 12 is rigid and has a non-expanded configuration presenting a smooth, uniform profile facilitating passage through a body cavity wall with an initial external diameter or cross section that is uniform along the length of the cannula distally of housing 14. Universal seal 16 is in the closed position with inner bends 78 biased into contact with one another to close variable size passage 69.

When it is desired to use endoscopic portal 10 to provide a passage through a body cavity wall, a penetrating member or obturator, such as a trocar T, is inserted through universal seal 16 as shown in FIG. 11 causing the variable size passage 69 to open or enlarge to receive the trocar T. Accordingly, universal seal 16 will be in an open position with the cross sectional size of passage 69 enlarged to receive the trocar T with the seal 16 exerting a compressive sealing force on the trocar T in the manner of a sphincter while the sleeve 18 remains in the normal non-expanded position with slit 32 closed as shown in FIG. 12. The compressible member 62 will be compressed and the spine members 66 will be deflected due to introduction of trocar T, and the compressible member 62 and the spine members 66 cause the inner bends 78 to sealingly contact the trocar T along the periphery or circumference thereof such that fluids cannot pass through the endoscopic portal. Seal 16 can be compressed a finite maximum amount by an instrument or object in variable size passage 69 without causing slit 32 in sleeve 18 to open. Accordingly, the variable size passage 69 can be enlarged to a maximum cross sectional size without sleeve 18 being moved to the expanded position. Therefore, instruments or objects having cross sectional sizes up to the maximum cross sectional size can be introduced in the variable size passage 69 in sealing relation with seal 16 while the sleeve 18 remains in the normal non-expanded position. Depending on the size of the trocar, there will not be any gaps or spaces between the inner membrane section 68 and the trocar T such that the membrane 64 will sealingly engage trocar T entirely along the periphery or circumference thereof or there may be small gaps or spaces between the inner membrane section 68 and the trocar T along the periphery of the trocar. However, even where small gaps are present, leakage of fluid through the endoscopic portal 10 will still not occur due to the small cross sectional size of any gaps in relation to the length of the seal 16. It should be appreciated, therefore, that the variable size passage 69 does not have to be completely closed in the initial position for seal 16 since fluid will not leak through a slightly open variable size passage over the relatively greater length of the seal 16.

Figure 13:
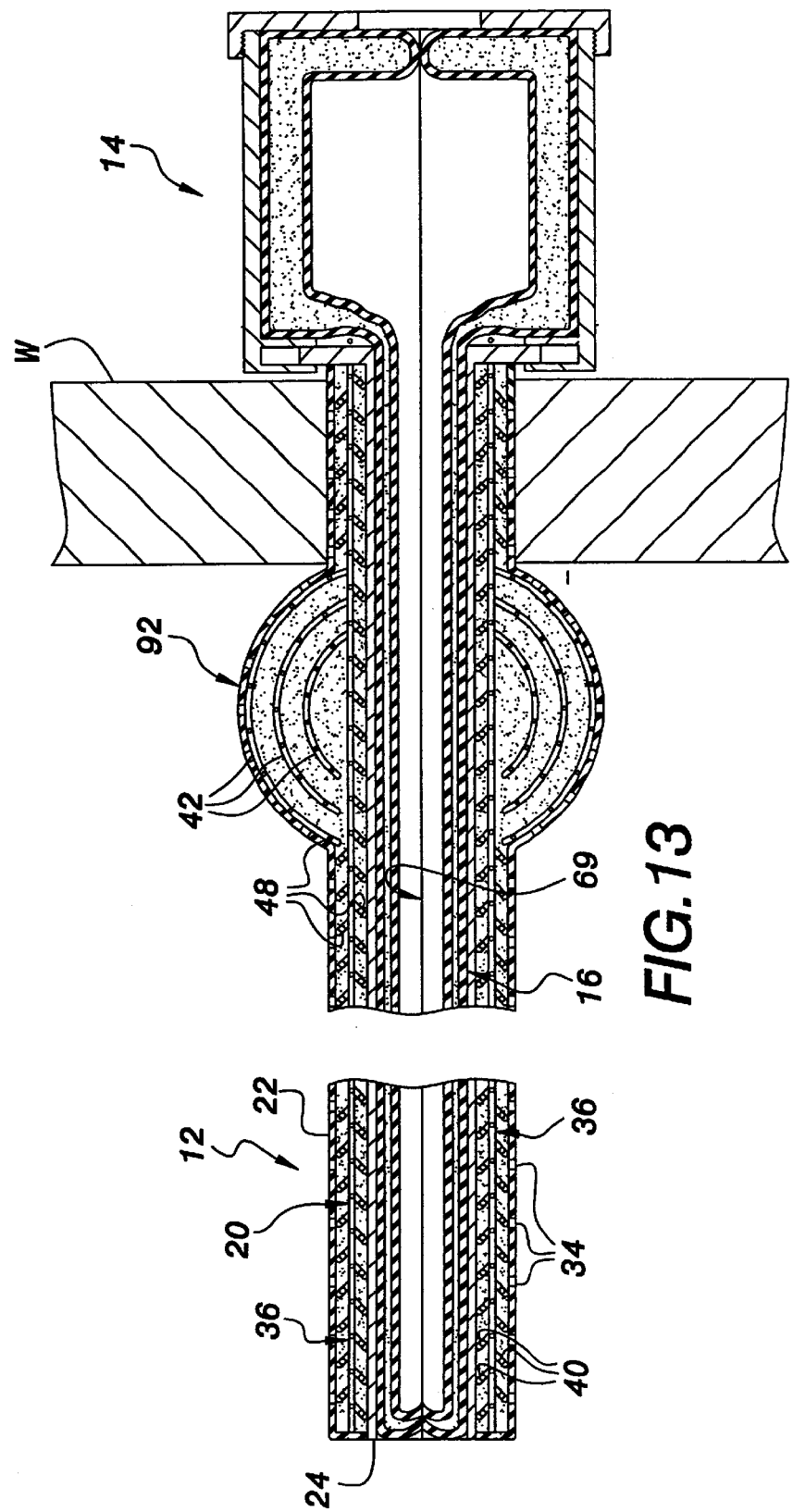
FIG. 13 is a broken, side sectional view of the endoscopic portal showing the cannula in the expanded configuration extending through a cavity wall with the liner in the closed position upon withdrawal of the trocar.

When the trocar T is fully inserted through the endoscopic portal 10, a distal tip of the trocar T protrudes beyond the distal end 24 of cannula 12 for use in penetrating a body cavity wall. The distal tip of the trocar T is forced through the body cavity wall creating a small size opening or puncture, and the cannula 12 follows the trocar T through the cavity wall to position the distal end 24 within the body cavity as shown in FIG. 13. Accordingly, the opening or puncture formed in the cavity wall corresponds in size to the cross sectional size of the cannula in the non-expanded configuration with the absorbent member in the dry state. The absorbent member 20 absorbs body fluids of the cavity wall W, as permitted by perforations 34 in membrane 22, as the cannula 12 passes therethrough and upon entry of the cannula in the body cavity. Where there is insufficient body fluid to place the absorbent member 20 in the wet state, fluid can be supplied to the absorbent member 20 from externally of the body cavity via port 44 and the associated spine member 36 having holes 48. Once in the wet state, the absorbent member 20 expands diametrically or in a direction transverse or radial to the longitudinal axis of cannula 12, and the spine members 36 return to the normal extended configuration due to softening of the absorbent member 20. Accordingly, the cannula 12 will have an expanded configuration with an external diameter or cross section greater than the external diameter or cross section of the non-expanded cannula configuration. With the absorbent member 20 in the wet state, straight branches 40 pivot outwardly and curved branches 42 spring outwardly from trunk 38 as shown in FIG. 13. Curved branches 42 form a rounded protuberance, bulge or bubble 92 at a predetermined location along cannula 12, the protuberance 92 being distally spaced from housing 14. The absorbent member 20 can be designed for greater expansion at the location of protuberance 92 in response to absorption of fluid and/or the absorbent member 20 can be mechanically expanded by curved branches 42. Distally and proximally of protuberance 92, the cannula 12 has a uniform or substantially uniform external diameter, greater than the initial external diameter thereof in the non-expanded configuration. Accordingly, the external diameter or cross section of cannula 12 in the expanded configuration is non-uniform along the length thereof, distally of housing 14. The protuberance 92 is disposed adjacent an internal surface of the cavity wall W with the cavity wall W being disposed between the protuberance 92 and the housing 14. Protuberance 92 prevents backing out of the cannula 12 from the body cavity and forms a stabilizer for the endoscopic portal 10 while housing 14 prevents the cannula from entering too far into the cavity. The portion of cannula 12 extending through the cavity wall W forms a seal along the length of the puncture or opening, i.e. along the thickness of the cavity wall W, due to expansion of cannula 12, and the opening in the cavity wall W will stretch non-traumatically to accommodate the larger external diameter or cross sectional size of cannula 12. Fluid such as insufflation gas and/or medicaments can be introduced in the body cavity via port 44 and the associated spine member 36, where the associated spine member 36 is provided without holes 48, and fluid can be introduced in the body cavity through seal 16 upon withdrawal of trocar T therefrom. Once the distal end 24 of cannula 12 is positioned in the body cavity, the trocar T is withdrawn from the endoscopic portal 10, and the seal 16 automatically returns to the closed position in the manner of a sphincter due to the bias of spine members 66 and compressible member 62 on inner membrane section 68 as shown in FIG. 13.

Various instruments of diverse sizes can be introduced in the body cavity and various size instruments and objects can be withdrawn from the body cavity through the endoscopic portal 10 in accordance with the procedure to be performed. FIG. 14 illustrates an instrument I, having a cross sectional size larger than the cross sectional size of trocar T, introduced through the endoscopic portal 10 to position a distal end of the instrument I in the body cavity while a proximal end of the instrument I remains externally of the body cavity. As with trocar T, instrument I is introduced in universal seal 16 causing the seal 16 to move from the normal closed position to the open position to enlarge the variable size passage 69 to accommodate the instrument I. The inner membrane section 68 sealingly contacts the instrument I entirely or substantially entirely along the periphery or circumference thereof to form a seal therewith while the sleeve 18 remains in the normal non-expanded position with slit 32 closed, since the cross sectional size of instrument I does not exceed the maximum cross sectional size to which variable size passage 69 can be enlarged without expanding the lumen of sleeve 18.

Instrument I is illustrative of a cutting instrument that can be utilized to excise anatomical tissue or structure, such as an organ, within the body cavity. The excised organ, for example the gall bladder, can be withdrawn from the body cavity through the endoscopic portal 10; and when the size of the excised organ exceeds the maximum cross sectional size to which variable size passage 69 can be enlarged without expanding the lumen of sleeve 18, the sleeve 18 will have to be moved to the expanded position to increase the size of the sleeve lumen to accommodate further diametric expansion of seal 16 and further enlargement of variable size passage 69 to receive the organ. The organ can be introduced in the variable size passage 69 directly to move sleeve 18 to the expanded position, or the organ can be withdrawn through a tubular expander introduced in the variable size passage 69 to open seal 16 and expand sleeve 18. FIG. 15 illustrates a tubular expander E, having a lumen with a cross sectional size large enough to accommodate the excised organ O, introduced in variable size passage 69 as described above for introduction of trocar T and instrument I. Introduction of tubular expander E in variable size passage 69 causes spine members 66 to pivot or deflect such that trunks 84 are no longer oriented radially with respect to the longitudinal axis of seal 16. Compressible member 62 is compressed and pleats 72 are pivoted or deflected to accommodate the tubular expander E in the variable size passage 69. Accordingly, sleeve 18 is moved from the normal non-expanded position to the expanded position with slit 32 are no longer oriented radially with respect to the longitudinal axis of seal 16. Compressible member 62 is compressed and pleats 72 are pivoted or deflected to accommodate the tubular expander E in the variable size passage 69. Accordingly, sleeve 18 is moved from the normal non-expanded position to the expanded position with slit 32 being opened to increase the diameter or cross sectional size of the sleeve lumen to accommodate the seal 16, which also expands diametrically. Seal 16 forms a seal with the tubular expander E, and the organ O is withdrawn from the body cavity through the lumen of the expander E. Instruments can be introduced in and withdrawn from the body cavity through the tubular expander, which accommodates instruments larger in size than the maximum cross sectional size to which the variable size passage can be enlarged without expanding the lumen of the sleeve. Since the sleeve 18 is moved to the expanded position by expander E, the cannula will be mechanically expanded to a further expanded configuration wherein the diameter or cross sectional size of the cannula 12 will be further increased, and the cavity wall will stretch non-traumatically to accommodate the increased external diameter or cross sectional size of the cannula. Various instruments and other objects having cross sectional sizes greater than the maximum cross sectional size of the variable size passage prior to expansion of sleeve 18 can be introduced in and/or withdrawn from the body cavity through seal 16, with or without the use of an expander, due to expansion of sleeve 18 when the variable size passage is enlarged beyond the maximum cross sectional size.

The cannula 12 in the wet state can be used for various additional purposes including contacting and/or manipulating tissue in the cavity to improve access, visibility or maneuverability, to treat tissue, to apply pressure to control bleeding, to absorb blood 12 to be forcefully withdrawn through the cavity wall W. Alternatively, fluid can be evacuated from the absorbent member 20 via one or more spine members 36 provided with holes 48 and connected with ports 44. Evacuation of fluid from absorbent member 20 performs a "drying" function causing the absorbent member 20 to collapse, contract or compress such that the external size and/or configuration of cannula 12 is reduced for removal through the cavity wall.

FIG. 16 illustrates cannula 12 of endoscopic portal 10 in the cannula expanded configuration without spine members 36, in which case absorbent member 20 expands diametrically a greater amount along a portion of the length of cannula 12 to form protuberance 92 when the absorbent member 20 is in the wet state. Accordingly, the portion of absorbent member 20 corresponding to protuberance 92 can have a cell or pore density substantially greater than the cell or pore density of the remainder of the absorbent member 20. When the absorbent member 20 is in the wet state, the portion of absorbent member 20 corresponding to protuberance 92 will expand outwardly to a greater size due to the greater cell or pore density thereof while the remainder of the absorbent member 20 will expand outwardly to a lesser size.

Figure 17:
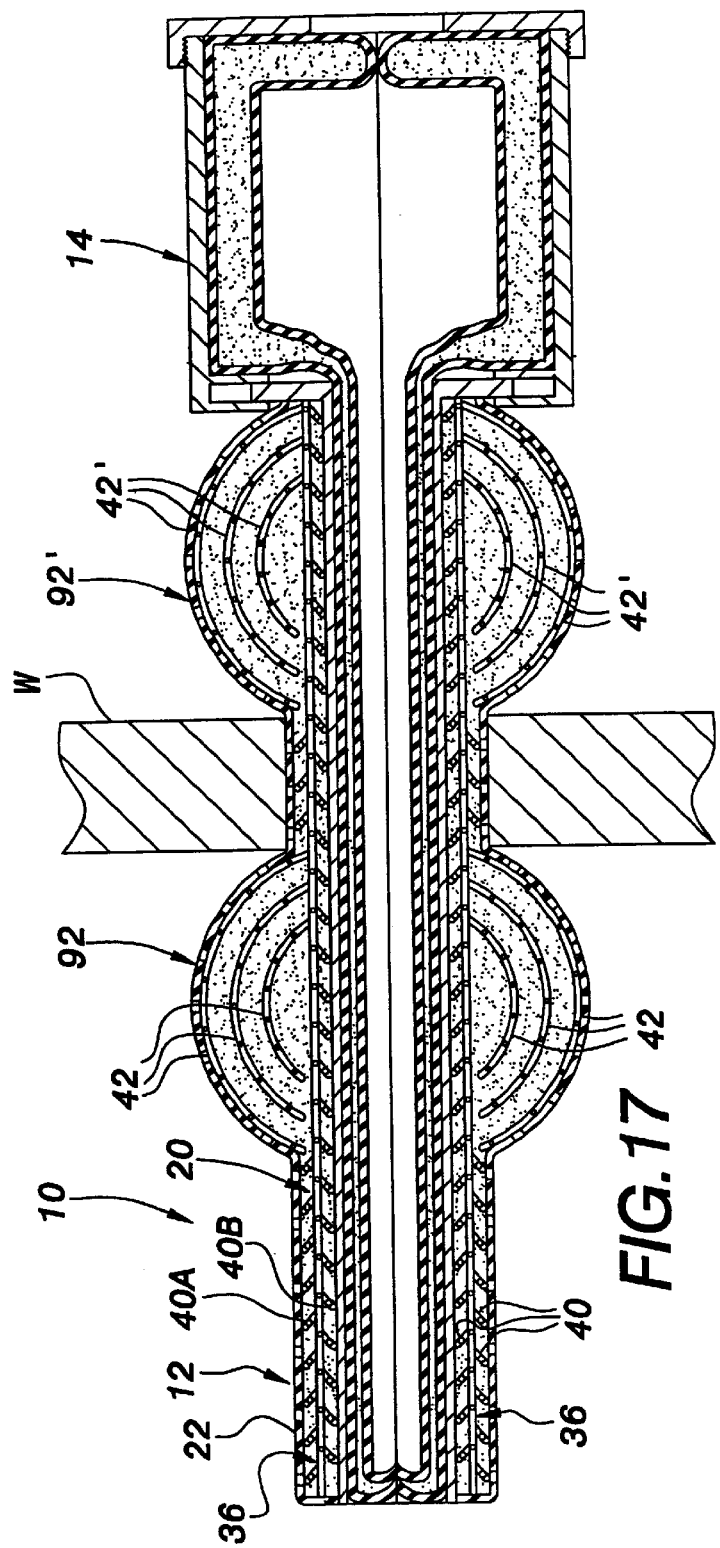
FIG. 17 is a broken, side sectional view of the endoscopic portal showing the cannula forming a plurality of protuberances in the expanded configuration.

FIG. 17 illustrates endoscopic portal 10 provided with a second protuberance 92', longitudinally spaced from protuberance 92 in the expanded configuration for cannula 12. Protuberance 92' is disposed just distally of housing 14 and protuberance 92 is distally spaced from protuberance 92' with the cavity wall W being held between the protuberances 92 and 92'. Spine members 36 include curved branches 42 defining protuberance 92 and a second set of curved branches 42' defining protuberance 92' with straight branches 40A and 40B between protuberances 92 and 92'. Protuberance 92 prevents cannula 12 from backing out of the body cavity while protuberance 92' prevents cannula 12 from moving farther than desired into the cavity. Since protuberance 92' is disposed externally of the body cavity, it is desirable that the absorbent member 20 be supplied with fluid actively such as via spine members 36 communicating with one or more fluid supply conduits or ports, such as port 44 shown in FIG. 2, disposed externally of the body cavity.

A modification of an endoscopic portal according to the present invention is illustrated at 110 in FIG. 18 wherein the absorbent member 120 is shown in the wet state. Spine members 136 disposed in absorbent member 120 provide longitudinally spaced protuberances 192 and 192' along cannula 112 when the absorbent member 120 is in the wet state. Each spine member 136 includes a trunk 138 extending longitudinally through absorbent member 120 and straight branches 140 and curved branches 142 extending from trunk 138. The trunks 138 of the spine members 136 are arranged, for example, at 45° spaced locations about the longitudinal axis of cannula 112 as shown in FIG. 19. Each spine member 136 has a normal extended configuration shown in FIG. 18 wherein straight branches 140 extend angularly, distally from trunk 138 in the direction of sleeve 118, the branches 140 being longitudinally spaced from one another along trunk 138 and being parallel with one another. Curved branches 142 defining protuberance 192 include an outer curved branch 142A curving outwardly from trunk 138, and inner curved branches 142B and 142C curving inwardly from outer branch 142A in the direction of sleeve 118. Branch 142A has a first end pivotally, resiliently or flexibly attached to trunk 138 and a second, free or unattached end adjacent trunk 138. Branches 142B and 142C have first ends pivotally, resiliently or flexibly attached to branch 142A, respectively, and second, free or unattached ends adjacent trunk 138. Curved branches 142 defining protuberance 192', which is proximally spaced from protuberance 192, include outer curved branch 142A', inner curved branches 142B' and 142C' and a curved branch 142D' disposed distally of outer branch 142A'. Branches 142A', 142B' and 142C' are similar to branches 142A, 142B and 142C. Branch 142D', which curves outwardly from trunk 138, has a first end pivotally, flexibly or resiliently mounted to trunk 138 and a second, free or unattached end adjacent trunk 138 with the second end of branch 142D' being disposed just proximally of or adjacent the first end of branch 142A'. For each spine member 136, the branches are disposed in the same plane as the trunk and such plane contains the cannula longitudinal axis. The branches 140 are pivoted toward trunk 138 and the branches 142 are compressed or flattened toward trunk 138 to be disposed close to or in substantial alignment with trunk 138 in the contracted configuration when the absorbent member 120 is in the dry state shown in FIG. 19. In the wet state for absorbent material 120, the spine members 136 return to the normal extended configuration with branches 142A, 142B and 142C of the spine members defining round protuberance 192 and branches 142A', 142B', 142C' and 142D' of the spine members defining pear-shaped protuberance 192' for cannula 12 in the expanded configuration. During use, one or both of the protuberances 192 and 192' can be introduced in the body cavity and the protuberances can be utilized to manipulate tissue or organ structure within the body cavity and/or to stabilize the endoscopic portal 110 relative to the body cavity wall.

Seal 116 for endoscopic portal 110 is different from seal 16 in that the inner membrane section 168 is not pleated along the cannula portion 158 and is pleated differently than seal 16 along the housing portion 160. Along the cannula portion 158, the inner membrane section 168 is cylindrical and tubular and is made of stretchable material as shown in FIG. 20 wherein only a short length of the cannula portion 158 is shown and wherein the outer membrane section 170 is not shown. The inner membrane section 168 is of relatively small diameter along the cannula portion such that the variable size passage 169 is closed or substantially closed along the cannula portion 158 in the normal closed position for seal 116. Along housing portion 160, the inner membrane section 168 is formed as a hollow cylinder or tube, made of a stretchable material or a non-stretchable material, larger in diameter than the inner membrane section along cannula portion 158 and compressed in the longitudinal direction to form a plurality of annular, accordion-like pleats 172 in series along the seal longitudinal axis. As shown in FIG. 18, each pleat 172 is defined by juxtaposed walls 174 connected to one another by an outer bend 176 and inner bends 178 connecting each wall 174, respectively, to the wall of an adjacent pleat, except for the distalmost inner bend, which connects the distalmost pleat to the cannula portion 158 of the inner membrane section 168, and the proximal most pleat which is connected to the outer membrane section 170. The outer bends 176 and the inner bends 178 circumscribe the cannula longitudinal axis. The walls 174 of pleats 172 are in contact with one another and the inner bends 178 are in contact with one another along the variable size passage 169 such that the variable size passage 169 is closed or substantially closed along the housing portion 160 in the closed position for seal 116. Compressible member 162 is disposed within the envelope defined by the inner and outer membrane sections 168 and 170, the compressible member being disposed between and around pleats 172 to maintain the closed position for seal 116.

Spine members 166 are disposed between the inner membrane section 168 and the outer membrane section 170 along cannula portion 158 and each spine member 166 has a wave-like configuration made up of a plurality of U-shaped segments 194 connected to one another at crests 195 as shown in FIG. 21. As shown in FIG. 18, U-shaped segments 194 are angled slightly in the distal direction, and the spine members 166 are made of a resilient, flexible or spring material to permit the spine members to bend, compress, flatten or deform when the seal 116 is opened. One or more of the spine members 166, which terminate proximally at the proximal end of sleeve 118, is provided with a tubular extension 196 extending proximally from the spine members into housing 114 to communicate with ports 144 connectable with a source of fluid or suction. Spine members 166 are embedded in the compressible member 162 and, together with the compressible member 162, maintain the variable size passage 169 in a closed or substantially closed position along the sleeve portion 158. As shown in FIG. 19, eight spine members 166 are provided in compressible member 162 at 45° spaced locations about a longitudinal axis of seal 116; however, any number of spine members can be provided. Accordingly, seal 116 is disposed in a normal closed position and is moved to an open position by an instrument introduced therethrough causing the variable size passage 169 to open to accommodate the instrument. When an instrument is introduced through seal 116, the inner bends 178 of inner membrane section 168 sealingly contact the instrument along the housing portion 160 and the inner membrane section 168 stretches to sealingly contact the instrument along the cannula portion 158 with the U-shaped segments 194 of the spine members 166 bending distally to accommodate the instrument in the variable size passage as shown in FIG. 29 for endoscopic portal 610. Upon removal of an instrument from seal 116, the seal automatically returns to the closed position preventing leakage of fluids through the endoscopic portal.

FIG. 22 illustrates a modification of the inner membrane section 168 wherein the inner membrane section 168 is compressed longitudinally along the cannula portion to form accordion-like pleats 172 such that pleats 172 extend along both the cannula portion 158 and the housing portion 160 with pleats 172 being smaller in diameter along the cannula portion 158 and being larger in diameter along the housing portion 160. It should be appreciated however, that the diameter of pleats 172 can be the same along the cannula portion and the housing portion.

FIGS. 23–25 illustrate various modifications of spine members for controlling the external configurations of the cannulas of the endoscopic portals in the cannula expanded configuration when the absorbent member is in the wet state. FIG. 23 illustrates a spine member 236 having a straight trunk 238 and curved branches 242 curving outwardly from trunk 238 in the normal extended configuration. Alternate branches 242 protrude from opposite sides of trunk 238, and each curved branch 242 is provided with a plurality of straight branches 240 extending outwardly from curved branch 242 in a direction away from trunk 238 in the extended configuration. Straight branches 240 are pivotally, resiliently or flexibly attached to curved branches 242. The curved branches 242 are compressed or flattened toward trunk 238 and the straight branches are pivoted toward the curved branches in the contracted configuration. Trunk 238 and branches 240 and 242 are tubular and are provided with holes 248.

FIG. 24 illustrates a spine member 336 having a straight trunk 338 and curved branches 342 protruding from trunk 338 in the extended configuration. Branches 342 are disposed in parallel planes, respectively, in the extended configuration and are spaced longitudinally from one another along trunk 338. Each branch 342 has first and second ends pivotally attached to trunk 338, and the branches 342 are pivotable toward trunk 338 to lie close to trunk 338 in the contracted configuration. Branches 342 can be of different sizes such as a large middle branch arranged between two smaller branches. The trunk 338 and the branches 342 are tubular and are provided with holes 348.

The spine member 436 illustrated in FIG. 25 comprises a straight trunk 438 and a curved branch 438 protruding outwardly from trunk 438 in the extended configuration. Branch 442 is disposed in the same plane as trunk 438 and has a first end pivotably, flexibly or resiliently attached to trunk 438 and a free or unattached second end adjacent trunk 438. A plurality of Y-shaped branches 440 extend outwardly from branch 442 in a direction away from trunk 438 and each Y-shaped branch 440 has an end or base pivotally, resiliently or flexibly attached to curved branch 442. Curved branch 442 can be compressed or flattened toward trunk 438, and branches 440 can be pivoted toward curved branch 442 in the collapsed configuration. The trunk 438 and the branches 440 and 442 are tubular and are provided with holes 448.

Another modification of an endoscopic portal according to the present invention is illustrated at 510 in FIG. 26. Endoscopic portal 510 is similar to endoscopic portal 10 except that seal 516 for endoscopic portal 510 does not have a cannula portion. Sleeve 518 for endoscopic portal 510 is made of a trimmable material allowing cannula 512 to be cut to a desired length prior to use. Absorbent member 520, membrane 522 and spine members 536 are the same as those for endoscopic portal 10, and FIG. 26 illustrates the absorbent member 520 in the dry state with spine members 536 in the contracted configuration. Seal 516 is substantially the same as seal 16 except that seal 516 is disposed within housing 514 and not within sleeve 518. Accordingly, seal 516 includes a housing portion but does not have a cannula portion. Prior to use, cannula 512 is trimmed or cut to a desired length; and, as shown in FIG. 27, cannula 512 has been cut just distally of curved branches 542 of spine members 536. When the cannula 512 is passed through cavity wall W to position the distal end 524 thereof within the body cavity, absorbent member 520 is hydrated to obtain the wet state therefor. Accordingly, straight branches 540 and curved branches 542 spring outwardly from trunk 538 and the spine members 536 will return to the normal extended configuration defining a protuberance 592 adjacent an internal surface of the cavity wall W. The cavity wall W will be positioned between the protuberance 592 and the housing 514 such that the cannula 512 is prevented from backing out of the cavity wall W and is prevented from entering the cavity too far. Seal 516 is disposed in the normal closed position with the variable size passage 569 therethrough 516 being closed or substantially closed, and the seal 516 is opened when instruments or other objects are introduced through the variable size passage into the lumen of sleeve 518. The slit 532 in sleeve 518 allows the lumen of the sleeve to be expanded to accommodate larger size objects resulting in further mechanical expansion of cannula 512 in the expanded configuration, the sleeve 518 being constrained from expanding when the absorbent member is in the dry state.

A further modification of an endoscopic portal according to the present invention is illustrated at 610 in FIG. 28. Endoscopic portal 610 is similar to endoscopic portal 110 except that cannula 612 includes a spring biased safety shield and the inner membrane section 168 of seal 616 is not pleated along the housing portion. The distal end 624 of sleeve 618 of cannula 612 terminates proximally of the distal ends of absorbent member 620 and membrane 622, which are aligned with one another. A safety shield 619 is concentrically disposed in absorbent member 620 distally of sleeve 618, and a helical coil spring 621, disposed concentrically around seal 616, is interposed between sleeve 618 and shield 619. Shield 619 terminates distally at a distal end 623 defining a blunt peripheral edge. Shield 619 is tubular or hollow and has an external diameter the same as the external diameter of sleeve 618 and an inwardly protruding annular shoulder 625 at the distal end 623. The distance that shoulder 625 protrudes inwardly from an internal surface 627 of shield 619 corresponds to the thickness of seal 616 when the seal 616 is compressed the finite maximum amount by an instrument introduced therethrough such that the shoulder 625 will engage the instrument. Spring 621 is connected to sleeve 618 and to shield 619 and biases shield 619 distally relative to sleeve 618 to an extended position wherein shield distal end 623 is disposed distally of the distal ends of absorbent member 620 and membrane 622. However, when the absorbent member 620 is in the dry state prior to use, the shield 619 is maintained or held in a retracted position, shown in FIG. 28, wherein the shield distal end 623 does not protrude beyond the distal ends of absorbent member 620 and membrane 622. As shown in FIG. 28, the shield distal end 623 in the retracted position is aligned with the distal ends of absorbent member 620 and membrane 622, which define a distal end for cannula 612. Shield 619 is maintained, held or constrained in the retracted position by absorbent member 620 in the compressed, dry state, the absorbent member being compressed around the sleeve, shield and spring such that the stiffness and rigidity thereof in the dry state prevents movement of the shield 619 to the extended position. If necessary, the absorbent member 620 can be attached, such as adhesively, to the sleeve 618 and to the shield 619. When the absorbent member 620 is hydrated and therefore in the wet state, the constraining force of the absorbent member 620 on shield 619 is released, and the spring 621 moves the shield 619 distally relative to the sleeve 618 to the extended position wherein the shield distal end 623 is disposed distally of the distal ends of absorbent member 620 and membrane 622.

Seal 616 is disposed within sleeve 612, housing 614 and shield 619 with a distal end of seal 616 disposed in abutment with shoulder 625 when the shield is in the retracted position. Seal 616 includes a uniform diameter tubular inner membrane section 668 along the sleeve portion and the housing portion defining variable size passage 669, and a plurality of spine members 666 which, together with compressible member 662, maintain the seal 616 in the closed position as shown in FIG. 28. Inner membrane section 668 and spine members 666 are similar to those of endoscopic portal 110 except that the U-shaped segments 694 of spine members 666 are larger in the housing portion than in the cannula portion. One or more of the spine members 666 are hollow and communicate with ports 644 at the proximal end of cannula 612.

FIG. 29 illustrates endoscopic portal 610 with a penetrating member or obturator, such as trocar T, introduced through variable size passage 669 of seal 616, it being noted that the distal portion of the cannula 612 is not shown in FIG. 29. Introduction of trocar T through seal 616 causes the seal 616 to be moved to the open position to enlarge variable size passage 669 to receive the trocar T. Spine members 666 are bent, deflected, compressed, deformed or flattened due to introduction of trocar T in variable size passage 669, and the inner membrane section 668 stretches to accommodate and sealingly engage the trocar T. The stretchable inner membrane section 668 exerts an elastic sealing force on the trocar T, and the compressible member 662 and the spine members 666 further bias the inner membrane section 668 into sealing engagement with the trocar T.

FIG. 30 illustrates the distal portion of the cannula 612 with the trocar T fully inserted therein such that a distal tip of the trocar protrudes beyond the distal end 623 of the cannula with the shield 619 held in the retracted position by the absorbent member 620 in the dry state. During penetration of the cavity wall W with the trocar T, the cannula 612 passes through the cavity wall W with the trocar T. As the cannula 612 passes through the cavity wall W, the absorbent member 620 absorbs fluids of the cavity wall W as permitted by perforations 634 in membrane 622. Once the distal end of cannula 612 and, therefore, the distal ends of the absorbent member 620 and membrane 622, have passed through the cavity wall W and entered the body cavity as shown in FIG. 31, the absorbent member 620 will be in the wet state with spine members 636 in the extended configuration and the shield 619 will be released for movement distally to the extended position by spring 621 such that the distal tip of the trocar T is protected. With the shield 619 in the extended position, the shield distal end 623 protrudes distally beyond the distal ends of the absorbent member 620 and membrane 622, and the distal tip of the trocar T is disposed within the shield. Upon removal of the trocar T from the endoscopic portal, the seal 616 automatically returns to the closed position as shown in FIG. 32 such that the variable size passage 669 is closed to prevent leakage of fluids therethrough. Insufflation gas can be supplied to the body cavity through seal 612 via opening of variable size passage 669 and/or through one or more of the ports 644 and the corresponding spine members 636. The shield 619 can have a slit 629 in the wall thereof extending the entire length of the shield to permit the lumen of shield 619 to be expanded along with the lumen of sleeve 618 when the absorbent member is in the wet state where the sleeve 618 is slit as previously described. It should be appreciated that where the absorbent member 620 is hydrated passively via absorption of body fluids, the rate of absorption can be selected such that shield 619 is released for movement to the extended position as soon as the distal ends of absorbent member 620 and membrane 622 have entered the body cavity. It should be further appreciated that the absorbent member 620 can be hydrated actively with fluid supplied from externally of the body cavity via one or more of ports 644 and the corresponding spine members 636 where the corresponding spine members 636 are tubular and provided with holes.

An additional modification of an endoscopic portal according to the present invention is illustrated at 710 in FIG. 33. Cannula 712 for endoscopic portal 710 includes absorbent member 720, a stretchable membrane 722 concentrically disposed around absorbent member 720, a passage defining member or spine member 736 disposed in absorbent member 720 and seal 716 disposed in spine member 736. Spine member 736 comprises a trunk 738 in the nature of an elongate helical coil spring 738 having a distal segment 731 and a proximal segment 733 having coils of uniform diameter or size and an intermediate segment 735 disposed between the distal and proximal segments made up of coils of larger diameter or size as shown in FIG. 34. The number and size of the coils of the distal, proximal and intermediate segments can vary in accordance with the external configuration desired for cannula 712 in the expanded configuration when absorbent member 720 is in the wet state, the intermediate segment 735 having a large diameter coil interposed between two smaller diameter coils which in turn are connected to the still smaller diameter coils of the distal and proximal segments 731 and 733, respectively. The spring 738 defines a passage or lumen longitudinally therethrough and has a distal end 724 for being positioned in a body cavity and a proximal end for being disposed externally of the body cavity with the distal end 724 being aligned or substantially aligned with the distal ends of absorbent member 720 and membrane 722 to define a distal end of cannula 712. A plurality of J-shaped branches 743 are attached to spring 738 and have straight first ends pivotably, flexibly or resiliently attached to the coils of spring 738 and second, free or unattached curved ends. The spine member 736 has a normal extended configuration wherein the coils of spring 738 are spaced longitudinally from one another to define a uniform cylindrical configuration or diameter along the distal and proximal segments 731 and 733, respectively, and a rounded, spherical protuberance 792 along the intermediate segment 735 with the branches 743 extending outwardly from spring 738 as shown in FIG. 34. The spine member 736 is maintained in a contracted configuration shown in FIG. 33 by the absorbent member 720 in the dry state. In the contracted configuration, the spring 738 is more tightly wound such that the coils thereof are in contact with one another with no spaces therebetween, and the coils of the intermediate segment 735 have the same diameter as the coils of the distal and proximal segments 731 and 733. In the contracted configuration, the branches 743 are pivoted or flattened toward the coils to be in substantial alignment therewith. A transverse flange 728 is provided at the proximal end of the cannula 712 and has an opening therein communicating with the lumen of spring 738. If desired, the endoscopic portal 710 can be provided with a housing 714 as shown in dotted lines in FIG. 33, and the housing 714 can contain seal 716. Since the coils of spring 738 are held adjacent or in contact with one another when the absorbent member 720 is in the dry state, the spring 738 has a length when the absorbent member is in the dry state that is less than the length of the spring when the absorbent member is in the wet state. Seal 716 is similar to seal 16 except that seal 716 does not have a housing portion. Seal 716 is concentrically disposed within the lumen or passage of spring 738 and extends the entire length thereof. The seal is disposed in a normal closed position wherein the variable size passage 769 therethrough is closed or substantially closed as shown in FIG. 35 to prevent leakage through the endoscopic portal 710.

Prior to use, absorbent member 720 is in the dry state constraining or maintaining the spine member 736 in the contracted configuration. When it is desired to utilize endoscopic portal 710 to provide a passage through a body cavity wall, cannula 712 is passed through a cavity wall W such as with a penetrating member or obturator introduced through variable size passage 769, to position the distal end 724 thereof within the body cavity and to position flange 728 in abutment with an external surface of the cavity wall W as shown in FIG. 35. If desired, the flange 728 can be provided with an adhesive for securing the flange 728 to the external surface of the cavity wall W. The absorbent member 720 absorbs body fluids as permitted by perforations 734 in membrane 722 and expands radially or diametrically as well as longitudinally. Once the absorbent member 720 is in the wet state, spine member 736 returns to its normal extended configuration as shown in FIG. 36. Accordingly, the coils of spring 738 unwind causing protuberance 792 to be formed adjacent an internal surface of the cavity wall W and causing the spring 738 to lengthen or elongate. Accordingly, the cannula 712 will lengthen in the longitudinal direction such that the cannula itself performs a shielding function to protect the distal tip of the penetrating member. Accordingly, the tip of the penetrating member can protrude beyond the distal end of the cannula 712 for penetration through the cavity wall W; and, upon entry in the body cavity, the tip of the penetrating member will be disposed within the cannula 712. It should be appreciated that the endoscopic portal 710 can be provided without the spine member 736 in which case the absorbent member 720 itself can be designed to form protuberance 792 and to lengthen in the longitudinal direction in the wet state.

FIG. 37 illustrates a modification of spine member 736 wherein the spine member is made up of an inner spring 738 and an outer spring 738 disposed concentrically around inner spring 738. Spine member 736 has a normal extended configuration wherein the coils of inner spring 738A are longitudinally spaced from one another and are of uniform diameter and wherein the coils of outer spring 738B are longitudinally spaced from one another and have a diameter greater than the uniform diameter of the inner spring coils. The coils of the outer spring 738B can be of a uniform diameter or a non-uniform diameter as shown in FIG. 37 wherein the outer spring 738B has a large diameter coil interposed between two smaller diameter coils. The inner spring 738A fits within the outer spring 738B and both the inner and outer springs are more tightly wound in the contracted configuration and the coils of the outer spring 738B can be disposed between the coils of the inner spring 738A in the contracted configuration. The inner and outer springs 738A and 738B are maintained in the contracted configuration by the absorbent member in the dry state and return to the normal extended configuration when the absorbent member is in the wet state. The inner spring 738A will unwind and thusly expand in the longitudinal direction to increase the length of the cannula, and the outer spring 738B will unwind to form a protuberance 792 along the cannula. The outer spring 738B has a length less than the length of the inner spring 738A and can be positioned at any location along the length of the inner spring in accordance with the desired location for protuberance 792. The springs 738A and 738B do not have branches; however, it should be appreciated that one or both of the springs can be provided with various configured branches in accordance with the external shape desired for the cannula when the absorbent member is in the wet state.

FIG. 38 illustrates another modification of spine member 736 wherein the spine member 736 is made up of two or more separate spring segments, 738A and 738B longitudinally aligned with one another and having branches 743. Spine member 736 has a normal extended configuration wherein the coils of spring segments 738A and 738B are spaced longitudinally from one another, the coils of spring segment 738A being of uniform external diameter and the coils of spring segment 738B being of non-uniform external diameter. Spring segment 738B has a large diameter coil between a plurality of smaller diameter coils to form a protuberance 792 when the absorbent member is in the wet state. Accordingly, the cannula can be made up of any number of spring segments of uniform and non-uniform external diameter arranged at various locations in accordance with a predetermined external configuration desired for the cannula in the expanded configuration when the absorbent member is in the wet state.

Another modification of an endoscopic portal is illustrated at 810 in FIG. 39, only a distal portion of the endoscopic portal 810 being shown. Cannula 812 for endoscopic portal 810 comprises a liner 816, an absorbent member 820 disposed over liner 816 and a stretchable membrane 822 disposed over the absorbent member 820. The liner 816 is in the nature of an elongate rolled member and includes a thin sheet or layer of nonbreakable, biologically compatible or inert material rolled about a longitudinal axis to form a spiral. The rolled member 816 has a conical or tapered distal end 824 configured to penetrate a body cavity wall and a variable size passage 869 extending longitudinally through the liner 816. The liner 816 has a normal closed or initial position where the variable size passage 869 is closed or substantially closed at distal end 824. The liner 816 is made of a resilient or spring material, such as plastic, to maintain the closed position therefor. However, since liner 816 is maintained or constrained in the closed position by the absorbent member 820 in the compressed, dry state, the liner does not have to be made of spring materials but can be made of non-spring materials such as paper, leather and silk. Since the liner 816 is constrained by the absorbent member in the dry state, the variable size passage 869 cannot be enlarged to receive an instrument when the absorbent member is in the dry state. Accordingly, the cannula 812 is self-penetrating. The absorbent member 820 extends the entire length of the liner 816, and the absorbent member can come to a sharp point at distal end 824 to facilitate penetration. Even where the absorbent member does not come to a sharp point, the cannula 812 can still be utilized to penetrate a cavity wall with the assistance of a small skin incision as permitted by the tapered configuration of the cannula distal end.

When the absorbent member 820 is hydrated and in the wet state, such as via absorption of body fluid through perforations 834, the liner 816 can unroll or unwind to enlarge variable size passage 869 to receive an instrument, and the absorbent member 820 in the wet state causes the liner 816 to sealingly engage the instrument. The liner 816 returns to its normal closed position after withdrawal of the instrument therefrom due to the resilience or force of the liner itself and/or due to the force of absorbent member 820 or an externally applied resilience or force. Accordingly, cannula 812 is representative of a cannula wherein the variable size passage is of a fixed cross sectional size when the absorbent member is in the dry state and is of variable cross sectional size when the absorbent member is in the wet state with the absorbent member in the wet state biasing the variable size passage to an initial cross sectional size while permitting the variable size passage to enlarge to a greater cross sectional size. Where the initial cross sectional size of the variable size passage is not sufficiently small to prevent leakage, a valve, such as a flapper or trumpet valve, can be utilized in the endoscopic portal.

Another modification of an endoscopic portal according to the present invention is illustrated in FIG. 40 at 910. Cannula 912 for endoscopic portal 910 includes a stretchable elastic sleeve or passage defining member 918, absorbent member 920 disposed around sleeve 918, stretchable membrane 922 disposed around absorbent member 920 and a liner 916 disposed in sleeve 918. Liner 916 includes a compressible member 962 defining a variable size passage 969 therethrough, and a spine including a plurality of spine members 966 disposed within compressible member 962 as shown in FIG. 41. Spine members 966 are in the nature of elongate, small diameter rods, wires or filaments made of resilient, flexible or spring material disposed in variable size passage 969 and within compressible member 920 to form a mesh. The spine members 966 are angled inwardly at their distal ends to define a conical or tapered distal end 924 of cannula 912 terminating at a tip for penetrating an anatomical cavity wall. The spine members 966 extend from the distal end to a proximal end of the sleeve 918 coupled with housing 914. Housing 914 has a hollow, truncated conical configuration with a rearward wall 954 formed by a stretchable, elastic membrane extending across the open rearward end of housing 914 as shown in FIG. 42. Membrane 954 has a small, enlargeable or expandable hole 956 therein aligned with variable size passage 969. Tubular conduits or channels 967 are disposed in compressible member 962 and extend longitudinally therethrough. Channels 967 are connected with ports 944 protruding from housing 914 and are provided with valves 946 for controlling fluid flow therethrough. Two ports 944 are provided in endoscopic portal 910 allowing one port to be used to supply fluid to absorbent member 920 and the other port to be used to evacuate or aspirate fluids from absorbent member 920.

Endoscopic portal 910 includes a directional control mechanism including a plurality of control wires 973 extending longitudinally through compressible member 962 and control wheels 975 for operating the control wires 973. The control wires 973 have distal ends connected to sleeve 918 and proximal ends connected to control wheels 975. The control wheels 975 protrude from housing 914 and are rotatable to wind and unwind the control wires 973 to selectively change the angular orientation of the distal end 924 of cannula 912 as shown in dotted lines in FIG. 40. The directional control mechanism can be like the adjustment system disclosed in applicant's prior application Ser. No. 08/287,007 filed Aug. 8, 1994 and incorporated herein by reference.

The passage defining member 918 has a normal non-expanded position wherein the rubber sleeve is relaxed or unstretched, and the sleeve 918 is prevented from expanding by the absorbent member 920 in the dry state. Liner 916 is disposed in the normal closed or initial position with compressible member 962 and rods 966 filling or substantially filling the variable size passage 969. With the absorbent member 920 in the dry state, an instrument cannot pass through the variable size passage 969 at distal end 924, and the tapered distal end 924 of cannula 912 allows the cannula in the dry state to be used to penetrate an anatomical cavity wall without the need for an obturator introduced through liner 916. During penetration of the cavity wall, absorbent member 920 absorbs body fluids as permitted by perforations 934 in membrane 922 such that the absorbent member 920 will be in the wet state. In the wet state, the distal end 924 of the cannula 912 becomes soft and blunt as shown in dotted lines in FIG. 40, and the control wheels 975 can be rotated to selectively wind or unwind the control wires 973 to adjust the angular orientation or position of the distal end 924. The cannula 912, which has functioned as a penetrating member or obturator, now functions as a cannula in that various size instruments can be introduced through the variable size passage 969. As shown in FIG. 41, introduction of an instrument I through variable size passage 969 causes the compressible material 920 to be compressed and the spine members or rods 966 to be deflected to accommodate the instrument I, and the spine members 966 contact the instrument I with the compressible material 920 biasing the spine members to contact the instrument. The variable size passage 969 can be enlarged to the maximum cross-sectional size without expansion of sleeve 918 and can be enlarged beyond the maximum cross-sectional size via expansion or stretching of sleeve 918 as permitted by the soft condition of the absorbent member in the wet state. The channels 967 can be utilized to supply fluid to or to withdraw fluid and other substances from the body cavity where the channels 967 protrude or pass through the membrane 922 at distal end 924 to communicate with the body cavity. Since fluid can pass between the rods 966, it is desirable that the endoscopic portal 910 include a valve in housing 914 to prevent fluid flow through the endoscopic portal.

Another modification of an endoscopic portal according to the present invention is illustrated at 1010 in FIG. 43. Cannula 1012 for endoscopic portal 1010 comprises an absorbent member 1020, a liner 1016 disposed in the lumen of the absorbent member and a stretchable membrane 1022 disposed around absorbent member 1020. Cannula 1012 is similar to seal 16 without the housing portion, since endoscopic portal 1010 is provided without a housing.

Liner 1016 is similar to the inner membrane section 68 of seal 16 and includes radial pleats 1072 disposed about variable size passage 1069 as shown in FIG. 44. Membrane 1022 is connected to liner 1016 at the distal and proximal ends of the absorbent member. Membrane 1022 is similar to the outer membrane section 70 of seal 16 except that membrane 1022 has perforations 1034. Accordingly, the membrane 1022 and the liner 1016 form an enclosed envelope or bag containing absorbent member 1020 with the material of the absorbent member being disposed between liner 1016 and membrane 1022 and between adjacent pleats 1072. A distal end of absorbent member 1020 has a configuration to penetrate an anatomical cavity wall and defines a distal end 1024 of cannula 1012. The distal end 1024 has a tapered or conical configuration terminating distally at a tissue penetrating tip. The membrane 1022 fits snugly over the dry absorbent member 1020, and the pleats 1072 of liner 1016 extend through the distal end 1024 as shown in dotted lines in FIG. 43. Accordingly, the pleats 1072 are of decreasing or diminishing radial size or length along distal end 1024.

Prior to introduction in the body, absorbent member 1020 is in the dry state such that the cannula 1012 is rigid and pencil-like. The liner 1016 is disposed in the initial position wherein variable size passage 1069 is closed as shown in FIG. 44. The variable size passage 1069 cannot be opened or enlarged as long as the absorbent member 1020 is in the dry state; however, by making the lumen of the absorbent member larger than the liner, the variable size passage can be enlarged in the dry state as explained for endoscopic portal 1210. With the absorbent member 1020 in the dry state, the cannula 1012 is used to penetrate a body cavity wall W to position the distal end 1024 within the body cavity while the proximal end of the cannula remains external of the body cavity. During passage through the cavity wall W and upon entry of the distal end 1024 in the body cavity, the absorbent member 1020 absorbs body fluid via perforations 1034. The absorbent member 1020 will then be in the wet state such that cannula 1012 expands diametrically in the expanded configuration, with or without formation of a protuberance, to form a seal along the thickness of the cavity wall W. The distal end 1024 of the cannula will become soft and blunt to protect tissue and organ structure within the cavity. The expanded absorbent member 1020 maintains the liner 1016 in the closed or initial position while permitting the variable size passage to be enlarged to receive an instrument. The absorbent member 1020 biases the liner 1016 into sealing engagement with the introduced instrument; and, when the instrument is withdrawn from the cannula, the absorbent member biases the liner to return to the initial position. If desired, one or more spine members, such as spine member 1036 shown in dotted lines in FIG. 44, can be provided in the absorbent member 1020 to bias the liner 1016 to the initial position and/or to control the external configuration of cannula 1012 in the expanded configuration, the spine member 1036 being similar to spine member 1066. When instruments are introduced through the variable size passage, the cannula will be expanded diametrically to a further expanded configuration.

FIG. 45 illustrates a modification of cannula 1012 wherein liner 1016 is scrunched into a lumen or recess of absorbent member 1020' to form random pleats or folds 1072' of different lengths. Pleats 1072' are illustrated as extending in a radial direction; however, it should be appreciated that the pleats 1072' do not have to extend radially in that the liner 1016 can be merely constricted, scrunched, crumpled, crushed or squeezed into the lumen of the absorbent member 1020'. FIG. 45 further illustrates formation of membrane 1022 integrally, unitarily with liner 1016' in that a portion of a unitary membrane is disposed in the absorbent member 1020' to form liner 1016' and another portion of the membrane is folded back over the absorbent member 1020' to form membrane 1022.

Another modification of an endoscopic portal according to the present invention is illustrated in FIG. 46 at 1110, the cannula 1112 for endoscopic portal 1110 being formed entirely as an absorbent member. Cannula 1112 includes an elongate absorbent member 1120 having a conical or tapered distal end 1124 terminating at a tip for penetrating an anatomical cavity wall and terminating proximally at a transverse flange 1128. The absorbent member 1120 has a lumen therethrough in the nature of a slit 1169 having a cross or cruciform shape extending longitudinally through the absorbent member 1120 as shown in FIG. 47. When the absorbent member 1120 is in the dry state, the variable size passage 1169 defined by slit 1169 is closed due to the rigidity and stiffness of the absorbent member. The distal end 1124 of the absorbent member is used to penetrate an anatomical cavity wall, and the absorbent member 1120 absorbs body fluids to be placed in the wet state. In the wet state, the cannula 1112 expands radially and longitudinally, and the distal end 1124 becomes rounded or blunt as shown in dotted lines in FIG. 46. The variable size passage 1169 can be expanded to receive an instrument introduced therethrough, with the absorbent member 1120 sealingly engaging the instrument in the variable size passage. The absorbent member 1120 returns the variable size passage 1169 to the initial position or size when the instrument is withdrawn; and, if desired, one or more spine members, such as spine member 1136 shown in dotted lines in FIG. 47, can be provided in the absorbent member.

Figure 48:
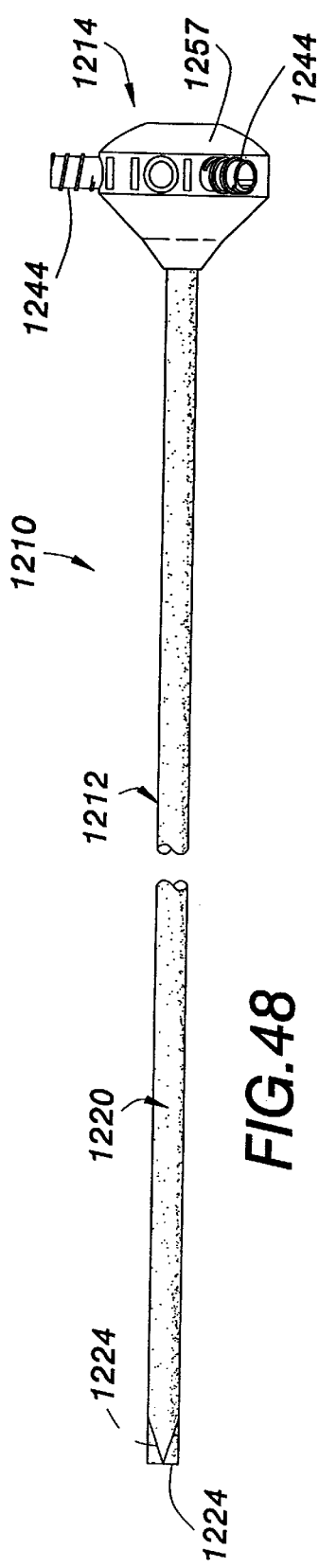
FIG. 48 is a broken side view of a further modification of an endoscopic portal according to the present invention showing the cannula in the non-expanded configuration.
Figure 49:
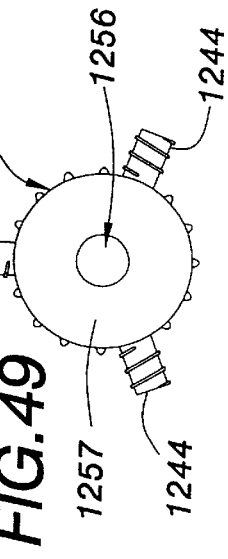
FIG. 49 is an end view of the endoscopic portal of FIG. 48.

Another modification of an endoscopic portal according to the present invention is illustrated in FIG. 48 at 1210. Endoscopic portal 1210 is similar to endoscopic portal 1010 except that cannula 1212 for endoscopic portal 1210 does not include an outer membrane and is connected with a head 1214. Cannula 1212 includes absorbent member 1220 having a blunt distal end 1224; however, the distal end can be configured to penetrate a body cavity wall as shown in dotted lines in FIG. 48. A proximal end of absorbent member 1220 is coupled to head 1214 which has a truncated conical configuration with an opening 1256 in rearward wall 1254, shown in FIG. 49, the opening 1256 being aligned with a lumen or passage extending longitudinally through absorbent member 1220. As shown in FIG. 51, three channels 1267 extend longitudinally through the absorbent member 1220 and have distal ends aligned with the distal end 1224 and proximal ends connected with ports 1244 protruding from head 1214. One port 1244 is utilized to supply fluid to the body cavity, another port 1244 is used for evacuation of fluid and substances from the body cavity and the third port 1244 can be used for supplying fluid to and/or evacuating fluid from the absorbent member 1220 in which case the channel 1267 associated with the third port 1244 is provided with holes. Liner 1216, shown in FIG. 51, is disposed in the lumen of absorbent member 1220 and is similar to liner 1016 except that pleats 1272 of liner 1216 do not diminish in size. A distal end of the liner 1216 terminates at distal end 1224, and a proximal end of the liner 1216 terminates at or within head 1214. The proximal and/or distal ends of the liner 1216 can be attached to the absorbent member 1220 or to the head 1214, and the opening 1256 in the rearward wall of the head is aligned with the variable size passage 1269 defined by liner 1216. The liner 1216 forms radial pleats 1272 uniformly spaced from one another and extending the same radial distance from the longitudinal axis of cannula 1212; however, the pleats 1272 can be non-radial and of random length and spacing.

Figure 50:
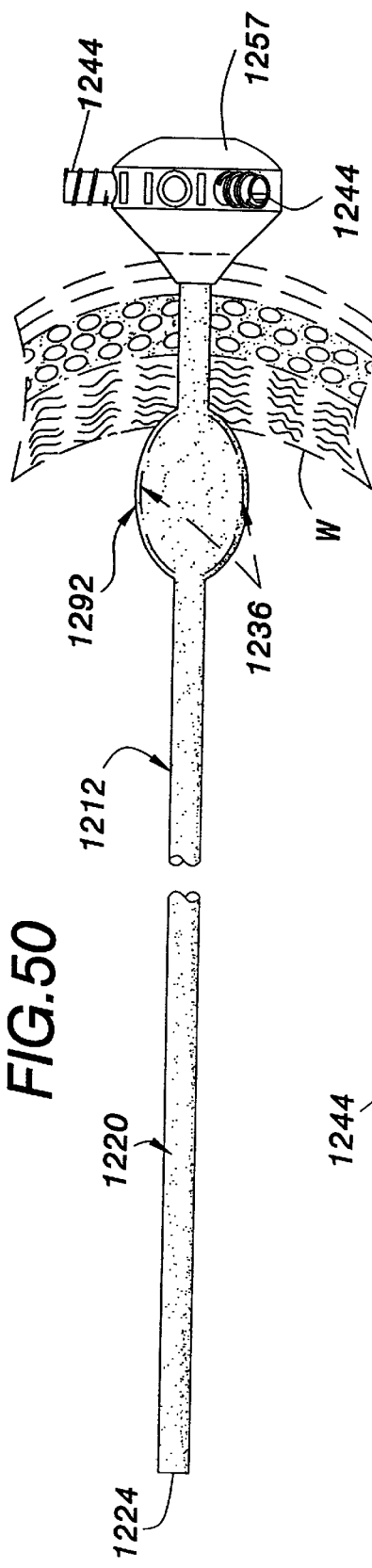
FIG. 50 is a broken side view of the endoscopic portal of FIG. 48 showing the cannula in the expanded configuration extending through a body cavity wall.

Prior to use, the absorbent member 1220 is in the dry state such that cannula 1212 has a non-expanded configuration. The lumen of the absorbent member 1220 through which the liner 1216 extends is large enough in the dry state to permit the variable size passage 1269 to be enlarged to receive an instrument, such as a Verress needle N shown in FIG. 52. Accordingly, even though the material of the absorbent member is disposed around the liner and between adjacent pleats 1272, the material does not completely fill the space around the liner such that the variable size passage 1269 can still be opened a finite amount when the absorbent member is in the dry state. Where the distal end 1224 is blunt as shown in FIG. 48, a penetrating member or obturator, such as Verres needle N, can be introduced through the variable size passage 1269 of liner 1216. As shown in FIG. 52, introduction of needle N in variable size passage 1269 causes the variable size passage to enlarge to accommodate the needle N in sealing relation. When the cannula 1212 is passed through a cavity wall W as shown in FIG. 50, the absorbent member 1220 absorbs body fluids and/or is supplied with fluid through one of the channels 1267 to obtain the wet state. As shown in FIGS. 50 and 52, the absorbent member 1220 expands diametrically or radially in the wet state such that the cannula 1212 has an expanded configuration with an external diameter or cross-sectional size larger than the diameter or cross-sectional size of the cannula in the non-expanded configuration. One or more spine members 1236, shown in dotted lines in FIG. 50, can be provided in the absorbent member 1220 to produce a protuberance 1292 in the wet state. Upon withdrawal of Verres needle N from cannula 1212, the liner 1216 is in an initial position due to the bias of absorbent member 1220; and, if desired, one or more spine members can be provided in the absorbent member to assist in biasing the liner to the initial position. Accordingly, the absorbent member 1220 maintains the variable size passage 1269 in a closed or initial position to prevent leakage through the endoscopic portal when no instrument passes therethrough while allowing the variable size passage to be enlarged from the initial position to receive instruments of various sizes in sealing relation.

With the endoscopic portals of the present invention, cannulas are provided comprising an elongate absorbent member having a variable size passage therethrough for receiving instruments in sealing relation. The variable size passage can be of fixed size in the dry state for the absorbent member and of variable size in the wet state for the absorbent member. Alternatively, the variable size passage can be of variable size in the dry state and in the wet state, with the passage enlargeable a finite amount in the dry state and enlargeable more than the finite amount in the wet state. The absorbent member expands radially in the wet state to form a seal along the thickness of the cavity wall and/or to form one or more protuberances for stabilizing the cannulas relative to a primary cavity wall and/or a secondary cavity wall disposed within the primary cavity for cavity within a cavity procedures. The absorbent member in the wet state maintains the variable size passage in an initial position, allows the variable size passage to be enlarged from the initial position to receive an instrument and biases the variable size passage to return to the initial position upon withdrawal of the instrument. Where the variable size passage is not closed sufficiently in the initial position, or while an instrument is in place, to prevent wall and/or a secondary cavity wall disposed within the primary cavity for cavity within a cavity procedures. The absorbent member in the wet state maintains the variable size passage in an initial position, allows the variable size passage to be enlarged from the initial position to receive an instrument and biases the variable size passage to return to the initial position upon withdrawal of the instrument. Where the variable size passage is not closed sufficiently in the initial position, or while an instrument is in place, to prevent fluid flow therethrough, conventional valves can be incorporated in the endoscopic portals. The distal end of the absorbent member in the dry state can be configured to penetrate an anatomical cavity wall allowing the cannulas to be used as a trocar or obturator; and, when the absorbent member is in the wet state, the distal end becomes soft and blunt. The absorbent member can expand longitudinally in the wet state to perform a shielding function. The cannulas can be provided with a safety shield, which can be designed as a modular component, maintained in a retracted position by the absorbent member in the dry state and released for movement to an extended position when the absorbent member is in the wet state.

The cannulas can be provided with or without an outer membrane; however, depending on the material of the absorbent member, an outer membrane can be beneficial in protecting the absorbent member and preventing any parts of the absorbent member from becoming detached in the body. The cannulas can be provided with or without a diametrically expandable passage defining member, which can include a slit or split sleeve, an elastic sleeve or a spine, for example. The passage defining member is maintained in a non-expanded position by the absorbent member in the dry state and is allowed to move to an expanded position when the absorbent member is in the wet state.

The endoscopic portals can include various types of liners including pleated and non-pleated membranes, rolled members, slippery coatings including spray on coatings, folded, scrunched or squished members, a mesh, overlapping or intermeshing leaves, rods, wires or filaments and a universal seal. Where coatings are utilized as the liner, the coatings can be dry in the dry state and becomes slippery in the wet state. One exemplary coating material suitable for use as the liner along all or part of the lumen of the absorbent member is Aquavene made by Menlo Care of Menlo Park, Calif. In order to reduce friction associated with introduction and withdrawal of instruments, the liner can extend less than the entire length of the endoscopic portals. The liners, which define the variable size passage, can be disposed in the cannulas and/or in a housing for the cannulas. Where disposed in the cannulas, the liners can extend the entire or less than the entire length of the cannulas. For example, the liners can be disposed at a proximal end of the cannulas, at a distal end of the cannulas or at intermediate locations along the cannulas. The liners can be segmented or discontinuous and can be disposed at more than one location. The absorbent member in the wet state biases the liner to the initial position when no instrument is received in the variable size passage and into sealing engagement with an instrument received in the variable size passage.

The universal seals and/or the tubular expanders can be designed in accordance with applicant's prior applications Ser. No. 08/618,328, filed Mar. 19, 1996 and Ser. No. 08/621,409, filed Mar. 25, 1996, the disclosures of which are incorporated herein by reference.

The absorbent member can be provided with various spine members for obtaining a predetermined external configuration or shape for the cannulas in the expanded configuration when the absorbent member is in the wet state and to add stiffness and rigidity to the absorbent member in the wet state. The spine members can be designed to provide one or more protuberances or bubbles along the cannula. The spine members can have various extended configurations to form various sizes and shapes of protuberances including spherical, pear-shaped and triangular shaped protuberances, for example. It should be appreciated that the absorbent member can be made of a non-expandable material in that the absorbent member does not have to expand in the wet state since the spine members can be used to obtain the expanded configuration for the cannulas. The spine members can be utilized to supply fluid to the absorbent member for hydration, to supply fluids and other substances to the body cavity, to evacuate fluid from the absorbent member to facilitate withdrawal of the cannulas from the body and to evacuate substances from the body cavity. Various medicaments or therapeutic agents can be introduced in the body cavity through the spine members.

The cannulas can be provided with channels therethrough for various purposes. Channels can be provided for supplying fluid to the absorbent member, evacuating fluid from the absorbent member, supplying fluid to the body cavity, supplying medicaments to the body cavity and evacuating substances from the body cavity. The fluid supplied to the absorbent member can be a medicament to be released in the body and can also serve the function of placing the absorbent member in the wet state. Separate channels can be provided for the various purposes, or the same channel can be used for more than one function.

The absorbent member can carry or be impregnated with various agents useful in the procedure to be performed. For example, the absorbent member can be impregnated or coated with medicaments or agents, such as anesthetics and coagulating agents, during manufacture such that the medicaments are carried, held or contained by or within the absorbent member in the dry state and are permitted to leak, leech or be released from the absorbent member in the wet state. In addition, medicaments and therapeutic agents can be supplied to the absorbent member and the patient's body via the channels and/or spines as discussed above. Accordingly, the cannulas can be utilized to deliver anesthetic allowing more procedures to be performed endoscopically under local anesthesia. Various coatings can be applied to the absorbent member to control porosity or frictional characteristic in desired locations as well as to protect the material of the absorbent member from damage due to stored springs and instruments, for example.

The speed of absorption of the absorbent member can be selected such that the cannula remains stiff and, where applicable, sharp, until the cavity wall is penetrated. Upon entry into the body cavity, the cannula is then in the expanded configuration due to the absorbent member being in the wet state. The tissue of the cavity wall expands or stretches non-traumatically to accommodate the expanded cannula and to accommodate further expansion of the cannula via mechanical expansion thereof, due to the introduction of instruments in the variable size passage. Accordingly, a puncture or opening can be formed in the cavity wall corresponding in size to the initial cross sectional size of the cannula, and the size of the puncture or opening can thereafter be enlarged non-traumatically due to expansion of the cannula. The absorbent member can be used to apply pressure to control bleeding during the procedure. The speed of absorption of the absorbent member can be selected such that the cannula expands longitudinally once penetration through the cavity wall is accomplished whereby the cannula serves as a shield to protect the tip of the obturator. Various instruments or other objects can be introduced into and/or withdrawn from the body cavity through the endoscopic portals, and the instruments and objects can be introduced and withdrawn through a tubular expander introduced in the endoscopic portal to enlarge the variable size passage. Introduction and withdrawal of instruments and objects through a tubular expander has the advantage of reducing friction associated with introduction and withdrawal of instruments directly through the variable size passage.

The cannulas can be provided with selectively locatable constrictors or collars as disclosed in applicant's prior application Ser. No. 08/578,876, filed Dec. 22, 1995, which is incorporated herein by reference. The constrictors can be different colors to serve as indicia identifying the location of constrained portions of the cannula. The cannulas can have externally visible bands or segments identifying the location of protuberances. In addition, a colored segment or band can be provided to indicate depth of penetration.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An endoscopic portal for providing a passage through a body cavity wall to provide access to a body cavity, comprising:

an elongate absorbent member for being introduced through the body cavity wall and having a distal end for being positioned in the body cavity, a proximal end for being positioned externally of the body cavity and a lumen between said distal and proximal ends defining the passage through the body cavity wall when the proximal end is positioned externally of the body cavity and the distal end is positioned in the body cavity to provide access thereto, said absorbent member having a dry state prior to introduction through the body cavity wall and a wet state upon introduction of said distal end in the body cavity, said absorbent member being rigid in said dry state and being soft in said wet state wherein, said absorbent member has a first cross sectional size in said dry state and a second cross sectional size, greater than said first cross sectional size, in said wet state and expands longitudinally in said wet state to increase the length of said absorbent member; and a valve disposed within the lumen and operative between a normally closed state and an opened stated, wherein in the opened state, the valve forms an opening sized and adapted to slidably receive an instrument such that the valve surrounds the instrument and maintains substantial contact with the instrument.

2. An endoscopic portal as recited in claim 1 and further including a spine disposed in said absorbent member for controlling the size and configuration of said absorbent member in said wet state.

3. An endoscopic portal as recited in claim 2 wherein said spine is tubular and has a distal end communicating with the body cavity and a proximal end connectable with a source of fluid for supplying fluid to the body cavity through said spine.

4. An endoscopic portal as recited in claim 2 wherein said spine is tubular and has a plurality of holes therein, said spine including a proximal end connectible with a source of fluid for supplying fluid to said absorbent member to obtain said wet state.

5. An endoscopic portal as recited in claim 1 and further including a membrane disposed around said absorbent member, said membrane including a plurality of perforations through which body fluid is supplied to said absorbent member to obtain said wet state.

6. An endoscopic portal as recited in claim 1 wherein said absorbent member includes a longitudinal axis and said membrane defines a plurality of different size pleats about said longitudinal axis.

7. An endoscopic portal as recited in claim 1 wherein said absorbent member includes a longitudinal axis and said membrane defines a plurality of accordion-like pleats along said longitudinal axis, each of said pleats having an outer bend circumscribing said longitudinal axis.

8. An endoscopic portal as recited in claim 1 further comprising a liner including a tubular membrane made of stretchable material.

9. An endoscopic portal for providing a passage through a body cavity wall to provide access to a body cavity comprising an elongate absorbent member for being introduced through the body cavity wall and having a distal end for being positioned in the body cavity, a proximal end for being positioned externally of the body cavity and a passage between said distal and proximal ends, said absorbent member having a dry state prior to introduction through the body cavity wall and a wet state upon introduction of said distal end in the body cavity, said distal end of said absorbent member being rigid and having a configuration in said dry state for penetrating the body cavity wall, said distal end of said absorbent member being soft and blunt in said wet state to prevent damage to internal anatomical tissue, said passage having a variable cross sectional size in said wet state to receive instruments of various cross sectional sizes in sealing relation; and a valve disposed within the passage and operative between a normally closed state and an opened stated, wherein in the opened state, the valve forms an opening sized and adapted to slidably receive an instrument such that the valve surrounds the instrument and maintains substantial contact with the instrument.

10. An endoscopic portal as recited in claim 9 wherein said absorbent member includes a longitudinal axis and said absorbent member expands in a direction transverse to said longitudinal axis in said wet state.

11. An endoscopic portal as recited in claim 9 wherein said absorbent member expands longitudinally in said wet state.

12. An endoscopic portal as recited in claim 9 wherein said absorbent member includes a sponge having a lumen therethrough defining said passage.

13. An endoscopic portal as recited in claim 9 and further including a membrane disposed over said absorbent member.

14. An endoscopic portal as recited in claim 13 wherein said membrane has a plurality of perforations therein through which body fluid is supplied to said absorbent member to obtain said wet state.

15. An endoscopic portal as recited in claim 9 wherein said passage is of fixed cross sectional size in said dry state.

16. An endoscopic portal as recited in claim 9 wherein said passage has an initial cross sectional size in said dry state, is enlargeable from said initial cross sectional size a finite amount in said dry state and is enlargeable from said initial cross sectional size more than said finite amount in said wet state.

17. An endoscopic portal for providing a passage through a body cavity wall to provide access to a body cavity comprising a cannula including an elongate absorbent member for being introduced through the body cavity wall and having a distal end for being positioned in the body cavity, a proximal end for being positioned externally of the body cavity and a passage between said distal and proximal ends through which instruments can be introduced, said absorbent member having a compressed dry state prior to introduction through the body cavity wall and an expanded wet state upon introduction of said distal end in the body cavity, said absorbent member having a first external cross sectional size in said dry state for being introduced through an opening in the body cavity wall corresponding in size to said first cross sectional size, said absorbent member having a second external cross sectional size, greater than said first cross sectional size, in said wet state such that said cannula dilates said opening and sealingly engages the body cavity wall along the thickness of the body cavity wall; and a valve disposed within the passage and operative between a normally closed state and an opened stated, wherein in the opened state, the valve forms an opening sized and adapted to slidably receive an instrument such that the valve surrounds the instrument and maintains substantial contact with the instrument.

18. An endoscopic portal as recited in claim 17 wherein said absorbent member has a predetermined external configuration in said wet state.

19. An endoscopic portal as recited in claim 18 wherein said absorbent member expands in said wet state and includes portions expandable to different sizes to obtain said predetermined external configuration.

20. An endoscopic portal as recited in claim 18 and further including a spine in said absorbent member having a normal extended configuration and maintained in a contracted configuration by said absorbent member in said dry state, said spine returning to said extended configuration when said absorbent member is in said wet state to shape said absorbent member to assume said predetermined external configuration.

21. An endoscopic portal as recited in claim 20 wherein said spine is tubular and is provided with a plurality of perforations, said spine being connectible with a source of fluid for supplying fluid to said absorbent member to obtain said wet state.

22. An endoscopic portal as recited in claim 17 wherein said absorbent member in said wet state permits said passage to be enlarged to different sizes to receive instruments of various sizes therethrough in sealing relation.

23. An endoscopic portal as recited in claim 22 and further including a liner in said absorbent member defining said passage.

24. An endoscopic portal as recited in claim 17 and further including a channel through said absorbent member communicating with the body cavity and connectible with a source of fluid for supplying fluid to the body cavity.

25. An endoscopic portal as recited in claim 17 and further including a channel through said absorbent member communicating with the body cavity and connectible with a source of suction for evacuating substances from the body cavity.

* * * * *